United States Patent [19]
Joskowicz et al.

[11] Patent Number: 5,343,385
[45] Date of Patent: Aug. 30, 1994

[54] INTERFERENCE-FREE INSERTION OF A SOLID BODY INTO A CAVITY

[75] Inventors: Leo Joskowicz, Bronx; Russell H. Taylor, Yorktown, both of N.Y.

[73] Assignee: International Business Machines Corporation, Armonk, N.Y.

[21] Appl. No.: 108,027

[22] Filed: Aug. 17, 1993

[51] Int. Cl.$^5$ ..................... G06F 15/46; G06F 15/20
[52] U.S. Cl. ..................... 364/167.01; 364/474.2; 364/461; 364/413.01
[58] Field of Search ............... 364/167.01, 474.2, 460, 364/461, 413.01, 413.31; 395/90, 904, 912, 924

[56] References Cited
U.S. PATENT DOCUMENTS

| | | |
|---|---|---|
| 4,704,686 | 11/1987 | Aldinger et al. |
| 4,436,684 | 5/1988 | White. |
| 4,837,703 | 6/1989 | Kakazu et al. ............ 364/474.2 |
| 4,888,707 | 12/1989 | Shimada ................ 364/474.2 |
| 5,006,991 | 4/1991 | Ohcoshi et al. ........... 364/474.2 |
| 5,056,031 | 10/1991 | Nakano et al. ........... 364/474.2 |
| 5,257,203 | 10/1993 | Riley et al. ............. 364/474.2 |

Primary Examiner—Jerry Smith
Assistant Examiner—Jim Trammell
Attorney, Agent, or Firm—Louis J. Percello

[57] ABSTRACT

The present method and apparatus determines an interference-free trajectory for fitting a moving solid body into a cavity, particularly where the body has a complex shape and tightly fits into the cavity. The method begins by describing the body surface with a finite set of body surface elements and the cavity surface with a finite set of cavity surface elements. Then a set of surface element pairs is determined. Each set comprises a body surface element and a corresponding cavity surface element. A neighborhood is a volume that contains the pair of surface elements but no other surface element pairs or parts of surface elements. Body motion constraints are developed for each pair. The constraints do not allow the body motion to cause the surface elements in the pair to interpenetrate or to leave their respective neighborhood. An incremental movement of the body, along a preferred direction, is then determined subject to the constraints. The body is moved the incremental amount and the process is repeated with a new set of pairs. Apparatus using the method can without interferences insert bodies into cavities or design and/or manufacture bodies and/or cavities with interference-free insertion trajectories. The invention has specific application to the design and insertion of prosthetic implants.

33 Claims, 13 Drawing Sheets

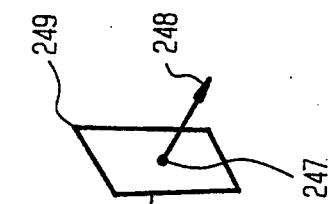
FIG. 2B.1
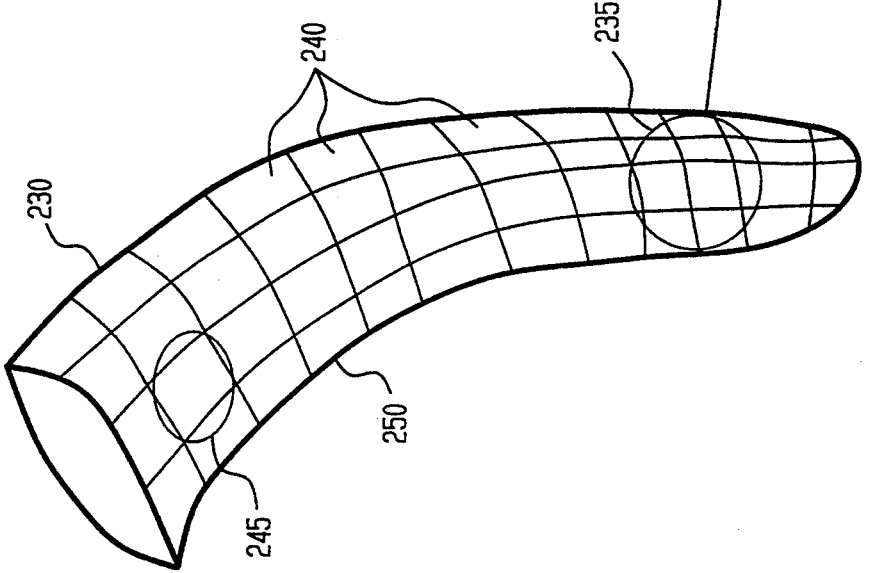
FIG. 2B
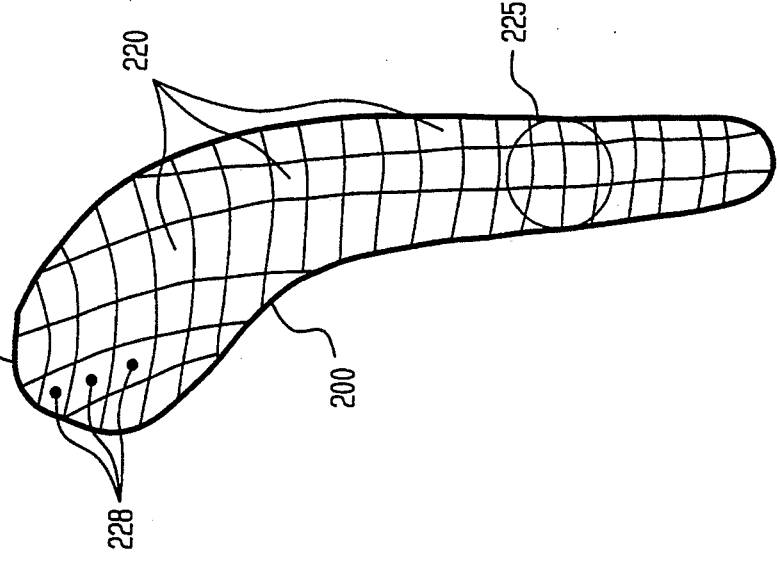
FIG. 2A
FIG. 2

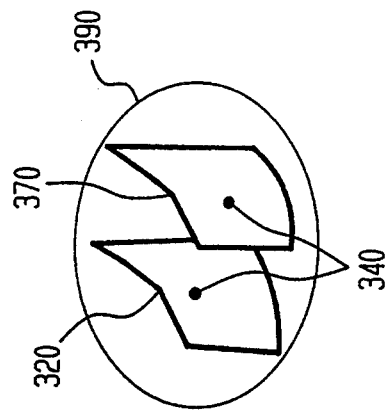

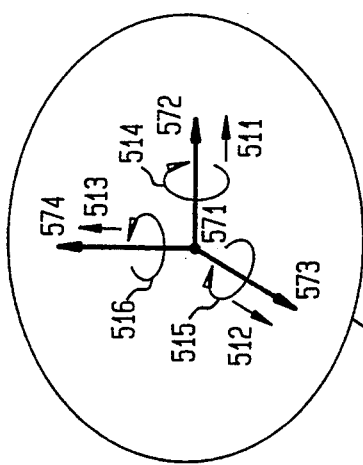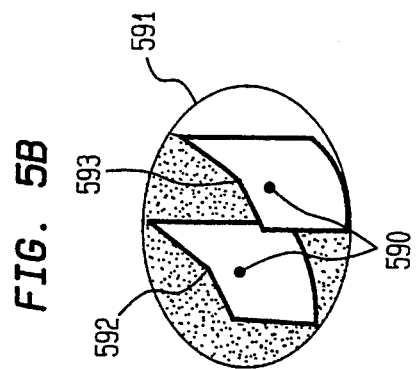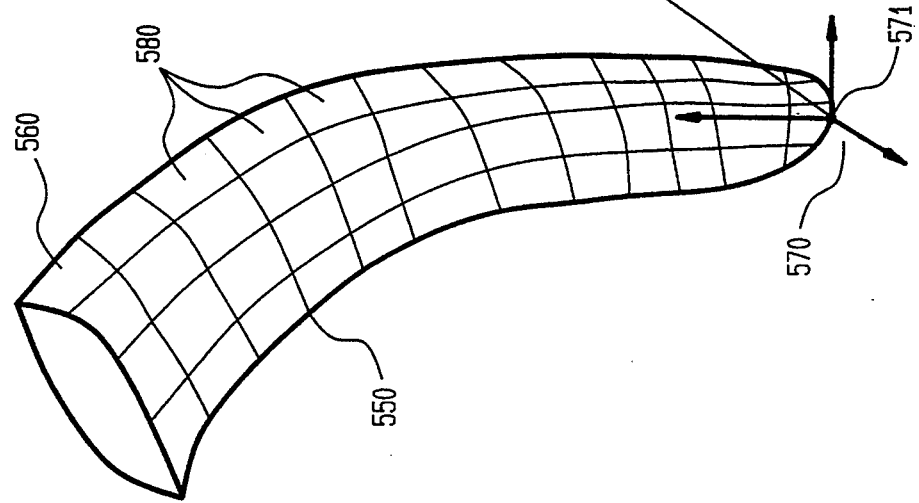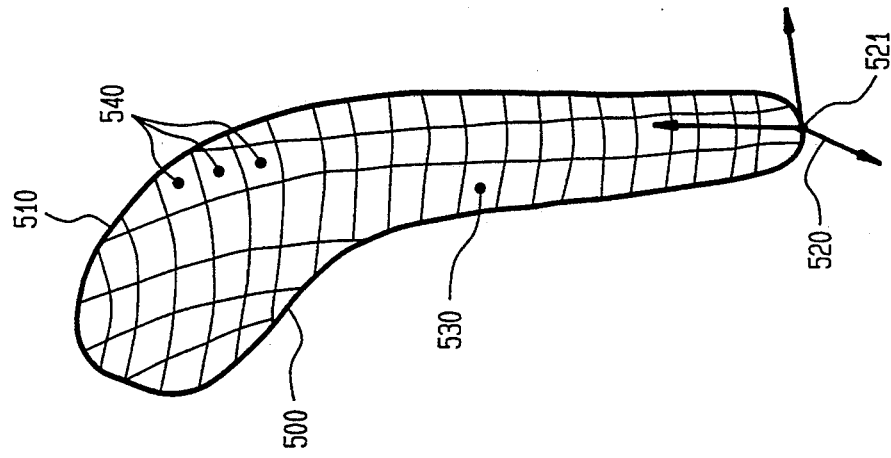
FIG. 5A
FIG. 5A.1
FIG. 5A.2
FIG. 5A.3
FIG. 5B

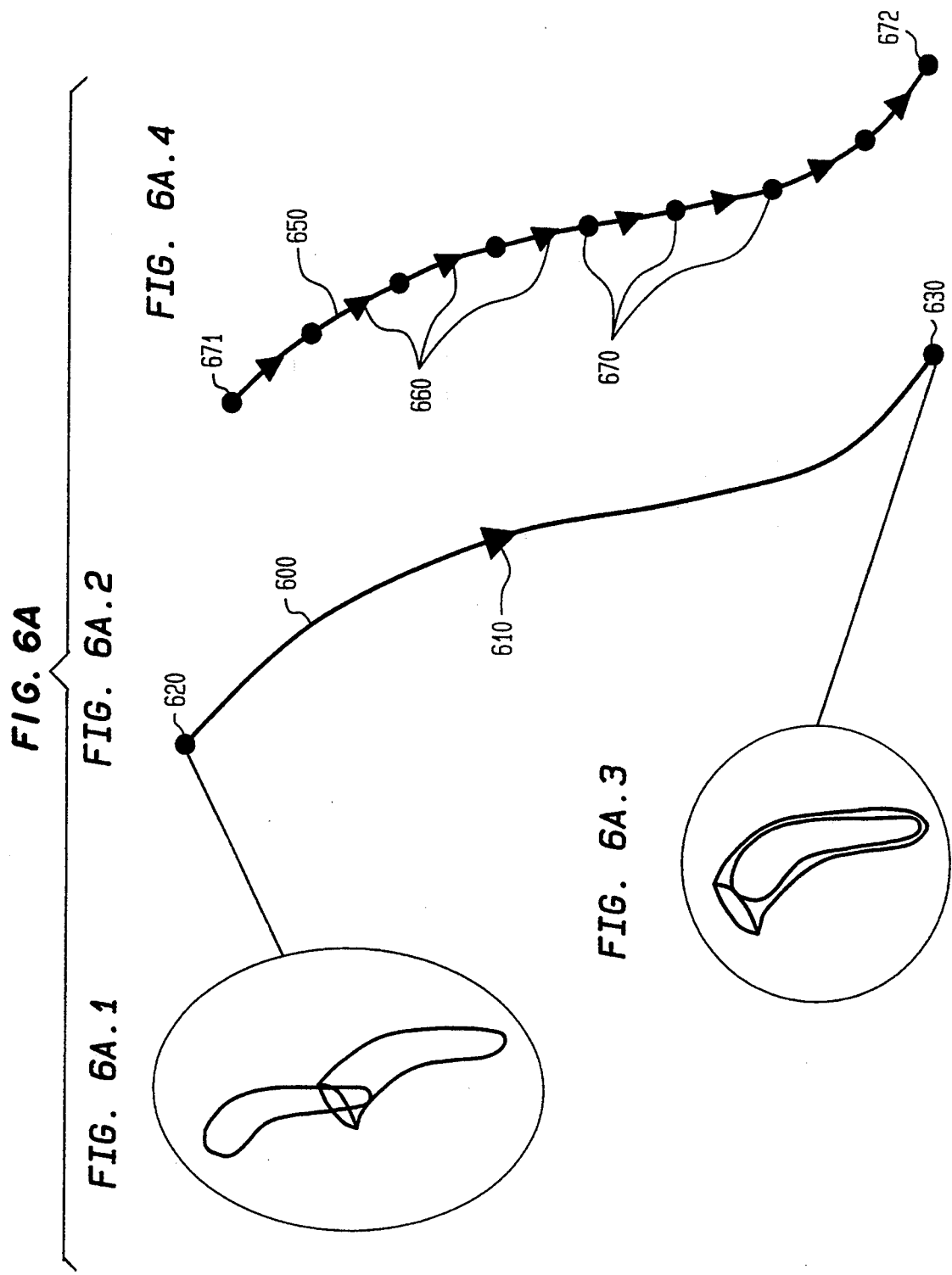

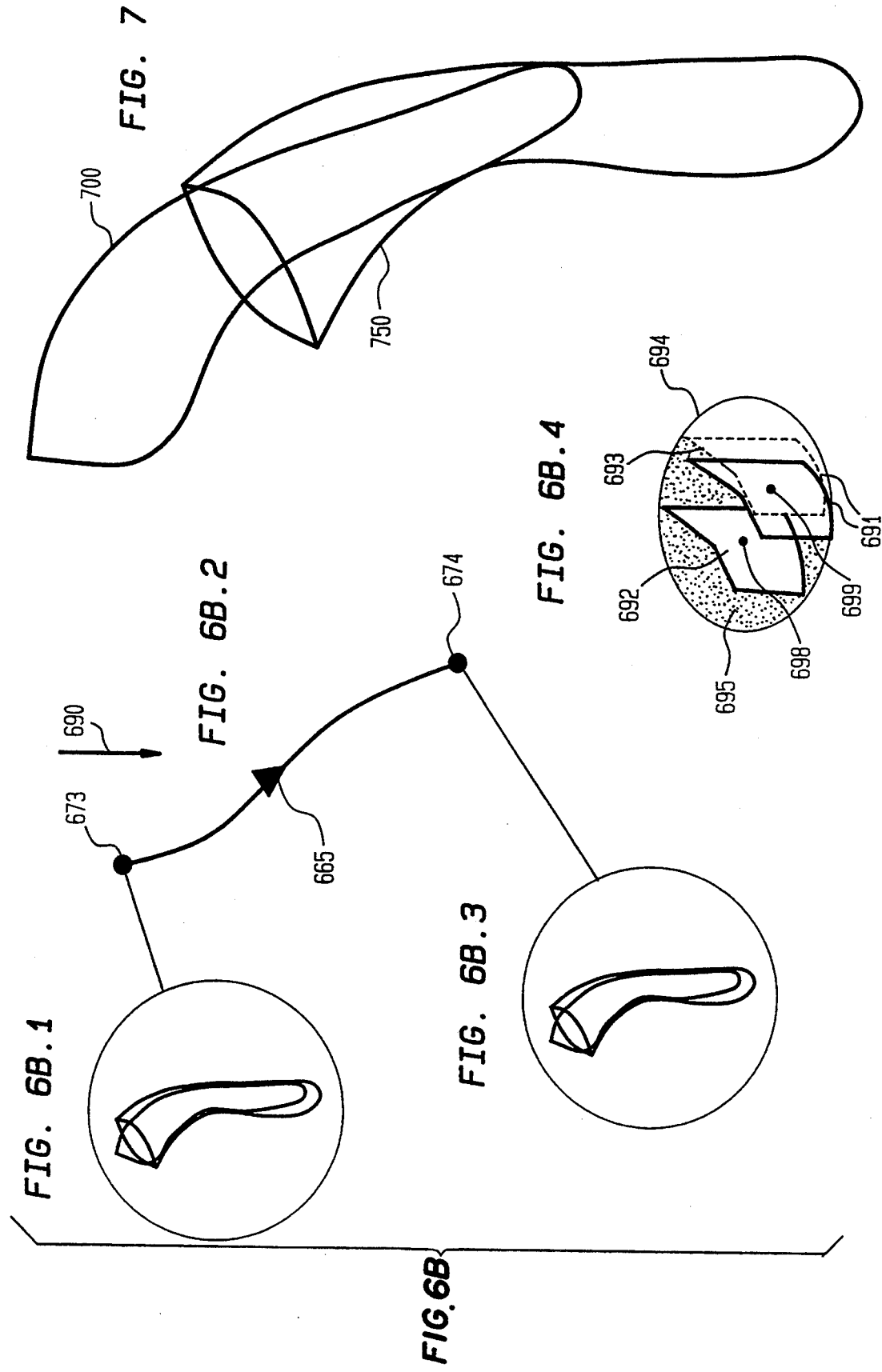

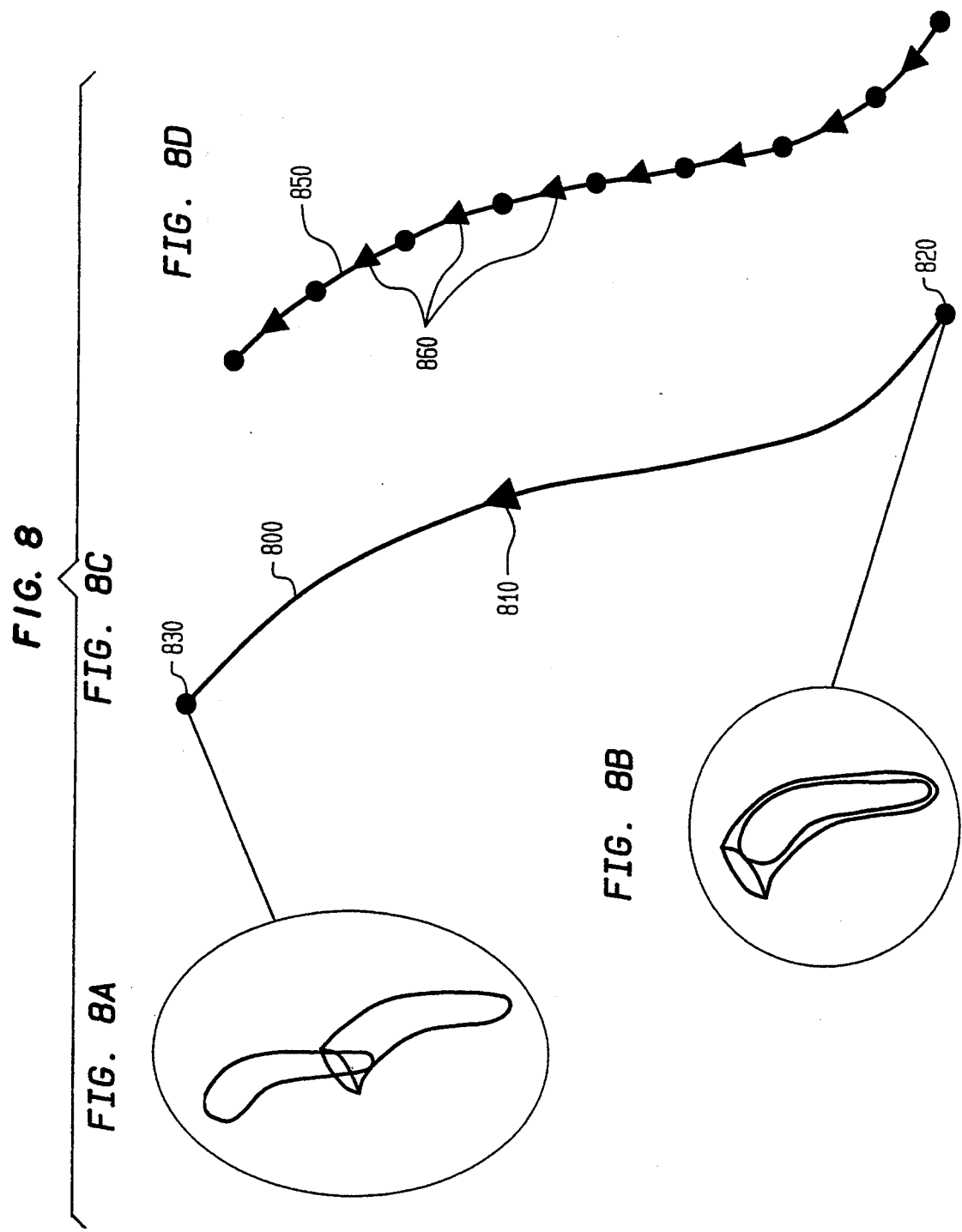

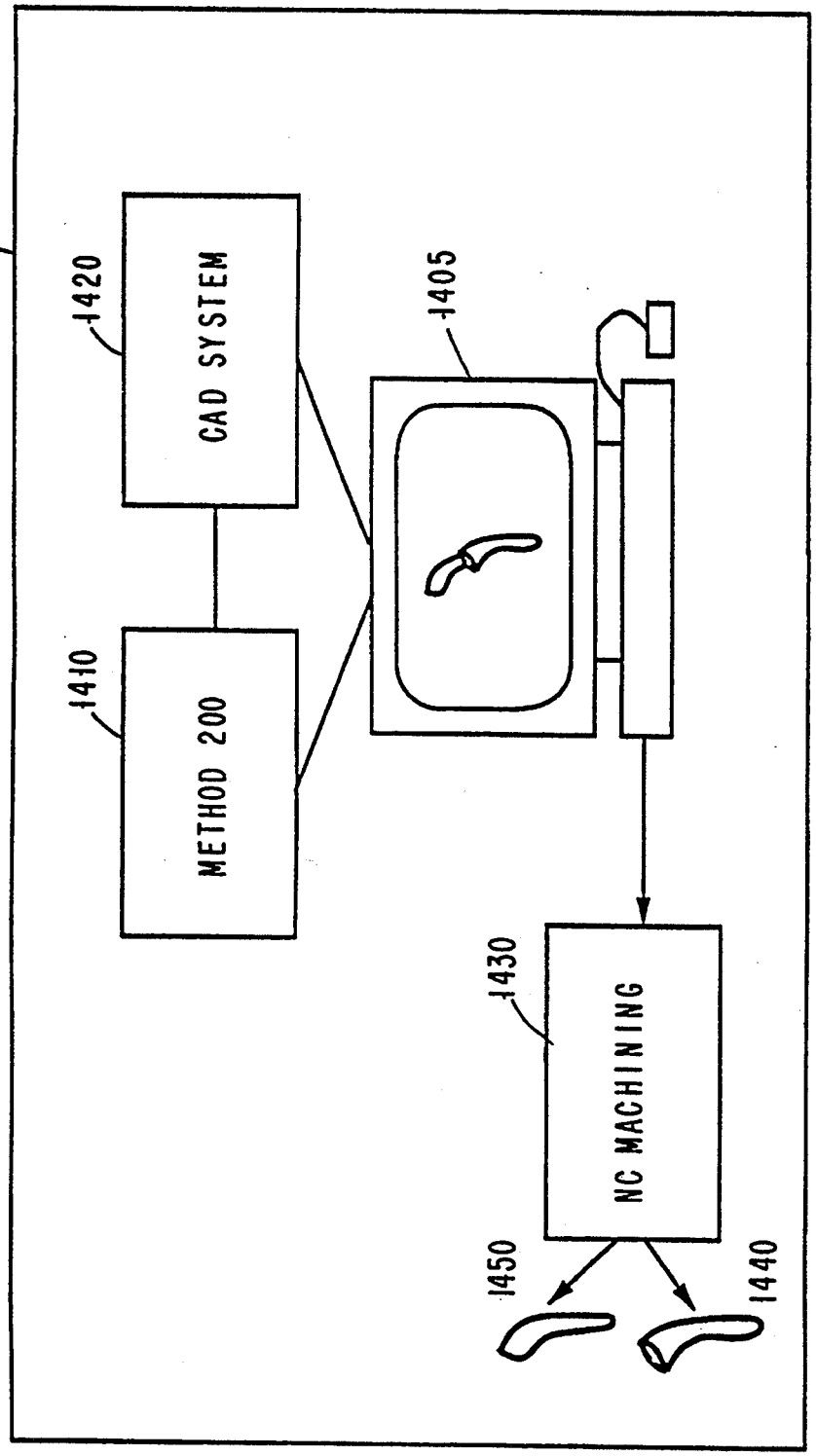

INTERFERENCE-FREE INSERTION OF A SOLID BODY INTO A CAVITY

FIELD OF THE INVENTION

This invention relates to the field of inserting a solid body into a cavity without encountering interferences. More specifically, the invention relates to inserting a prosthetic implant into an anatomical structure during reconstructive surgery.

BACKGROUND OF THE INVENTION

Moving a solid object from one location to another location without bumping or penetrating fixed obstacles on its way is a classical problem that has many applications in many fields. This problem is commonly called the motion planning problem (also called the path planning or the piano movers problem). In this problem, the goal is to find an interference-free (also called collision-free or non-overlapping) trajectory for a collection of moving objects amidst fixed obstacles from an initial to final configuration. An instance of the motion planning problem that is relevant here is the so-called "peg-in-hole" problem, in which a moving peg (the body) is to be inserted without interferences into a fixed hole (the fixed obstacle). Typically, the peg and the hole are tightly fit, so that the clearance between the peg and the hole is small and the peg and hole shapes are almost complementary. This requires fine motions to insert the peg into the hole. The interference-free insertion problem is related to the design and modifications of the peg and hole shapes such that the peg will not get stuck during its insertion inside the hole. A fundamental reference that formulates and describes solutions for this class of problems is *Robot Motion Planning* by Jean-Claude Latombe published by Kluwer Academic Publishers dated 1991, which is herein incorporated by reference in its entirety.

Solutions to the peg-in-hole problem have many applications in molding, manufacturing, assembly, medicine, and robotics, among others, in which a solid body is to be inserted or removed along a complex interference-free trajectory into a cavity. The analysis and solution of the interference-free insertion problem is used for designing tighter fits (force fits) for machine parts, for designing easily assemblable machines, for designing removable molds in part manufacturing, and for designing medical implants, among others.

There are basically two types of motion planning problems (including peg-in-hole): 1. those where the trajectory from the initial to the final configuration is known and 2. those where the trajectory is unknown and must be determined. In the first type of problem, the solid body trajectory from the initial to the final configuration has been determined beforehand; all is left is to verify that the trajectory is interference-free. This is done by testing for interferences between the moving body and the fixed obstacles at successive configurations along the trajectory. This solution is applicable to problems in which the trajectory is simple and can be easily determined from the shapes of the bodies. It is inapplicable for inserting a tightly fit body into a cavity because tight fit insertion requires many small incremental motions that can only be determined quantitatively from the body and cavity shapes.

The second type of problem, where the trajectory from the initial to the final configuration is unknown, covers the majority of motion planning problems, and in particular the interference-free insertion of a tightly fit body into a cavity. Some prior art finds an interference-free trajectory by searching the space of non-interference object configurations (the configuration space) for a continuous trajectory from the initial to the final configuration. The prior art discloses two strategies for searching this space—global strategies and local strategies. Global strategies first construct the configuration space and its connectivity graph and then search it for the desired trajectory. Local strategies directly search for the trajectory, performing geometric computations as the search progresses.

Global methods require computing the configuration space, whose complexity is polynomial in the geometric size of the objects and exponential in their total number of degrees of freedom. When the body and the cavity have tightly fit complex 3-dimensional shapes, the insertion trajectory requires thousands of small, incremental, coupled 6 degree of freedom motions (three translations and three rotations) to take the body from the starting to the final configuration. This makes global strategies and their variations (such as hierarchical configuration space decomposition, planning in low-dimensional configuration space projections, and exploiting the solid body geometrical regularities) impractical or inadequate. The configuration space corresponding to this problem is very large and complex, making its construction and search impractical.

Local strategies depend on the efficiency of the geometric computations and the effectiveness of the search strategy. Existing local strategies emphasize search effectiveness. Some prior art algorithms for a moving six degree of freedom polyhedron place a fine resolution grid on the configuration space and uses a set of heuristics based on the local configuration space geometry to search for the trajectory. For a tight fit, this method requires a very fine grid resolution and precise geometric computations which significantly affect the overall efficiency. Because of the fine grid resolution, very many small incremental motions from one grid point to the other are required to construct a trajectory from the initial to the final configuration. Other local strategies, such as the so-called potential field method or any strategy that repeatedly tests for object interferences as the trajectory is constructed are impractical as well. Because of the shape complexity, the interference tests are expensive. Further, many such tests are required because the fit between the shapes is tight, forcing the incremental motions towards the final configuration to be very small.

Solutions to the motion planning problem have applications in the medical arts, particularly in the design and manufacture of implants and the determination of implant insertion/removal trajectories. Computer-based medical imaging and modeling systems, coupled with computer-aided design and manufacturing technology, have already begun to have a major impact on the clinical practice of medicine. The design and fabrication of custom orthopedic implants from catscan (CT) data is one growing application of such systems. One class of implants, cementless implants, relys on a press fit, or tissue ingrowth, and significant surface-to-surface contact between the implant and the bone for fixation. The accuracy of bone preparation can have a significant effect on implant efficacy for these cementless implants.

Recent advances in robot bone machining have demonstrated an order-of-magnitude improvement in the accuracy of femoral canal preparation for hip replacement surgery. While improved implant design and fabrication and improved accuracy and consistency of bone preparation will greatly improve the surface-to-surface contact between the implant and the bone, i.e., the fixation, these improvements result from reduced tolerances that could restrict the insertion of the implant into the bone. Accordingly, improved methods and apparatuses must be made available to facilitate moving the implant along a correct trajectory so that the implant does not become stuck in the bone prior to reaching its final configuration.

To illustrate, in cementless hip replacement surgery, the damaged joint is replaced by an orthopedic implant which fits tightly into the femur. To install such implants, the surgeon typically starts by sawing off the femoral head and drilling a guide hole down the femur using a flexible reamer. The surgeon then drives a broach into the guide hole to make a cavity with the same shape as the implant. Since the broach shape matches the implant shape and the broach has been inserted into the cavity, there is some assurance that the implant will fit into the cavity carved by the broach. Unfortunately, the broach design may require the removal of bone which, for implant efficiency, would perhaps be better left intact. In summary, manually shaping the femur cavity with a broach allows a tight fit but still leaves undesirably large tolerances between the cavity and implant surfaces.

Robots can be employed to cut these cavity contours in the bone to attain a very tight fit (very small tolerances) between the implant and the cavity when the implant reaches its desired, final configuration in the bone. However, although the robot can machine a cavity with the desired shape within small tolerances, these small tolerances reduce the chance that the implant can actually be inserted into the cavity. It is highly undesirable discover this situation in the operating room. It would be much better to discover an insertability problem after the implant is designed and before it is fabricated. It is ever more desirable to identify a feasible insertion trajectory automatically, if one exists, and to identify possible places for design modification (of the cavity cut and/or implant shape) if such trajectory cannot be found.

OBJECTS OF THE INVENTION

An object of this invention is an improved method and apparatus for determining an interference-free insertion trajectory of a complex three-dimensional moving solid body tightly fitting into a cavity.

An object of this invention is an improved method and apparatus for designing and modifying body and cavity shapes so that the body can be inserted without interference into the cavity, maintaining a tight fit.

An object of this invention is an improved method and apparatus for inserting a solid body tightly fitting into a cavity with an interference-free trajectory.

Another object of the invention is an improved method and apparatus for analyzing, designing, and modifying tightly fit medical implants that are to be inserted in an interference-free trajectory into a cavity carved in an anatomical structure.

Another object of this invention is an improved method and apparatus for determining an interference-free trajectory for inserting a medical solid body implant into an anatomical structure and for inserting the implant into the structure along the determined trajectory.

SUMMARY OF THE INVENTION

The present invention is a novel method and apparatus for determining an interference-free insertion trajectory of a solid body tightly fitting into a cavity. The trajectory specifies how to move the solid body from an initial configuration (position and orientation) outside the cavity to a final configuration inside the cavity such that the body and the cavity do not interpenetrate at any time during the insertion. The method is best suited for tightly fit, complex 3-dimensional body and cavity shapes requiring complex insertion motions due to the small clearance between them. The invention is also a method and apparatus for inserting a solid body along an interference-free trajectory until the body reaches a final tight fit within a cavity. Further, the invention is a method and apparatus for designing and modifying body and cavity shapes so that the body can be inserted without interference into the cavity, maintaining a tight fit. The invention has a particular application in the analysis, design, modification, and interference-free insertion of medical implants into cavities carved in anatomical structures.

The method begins with the body in its initial configuration outside the cavity and the body and cavity surface shapes. It starts by describing the body and cavity surface shapes with a finite set of surface elements. Next, a set of surface element pairs is determined for the body configuration so that each surface element pair in the set comprises a body surface element and a corresponding cavity surface element. A surface element pair includes one surface element from the solid body and the surface element from the cavity which is closest to it. A neighborhood, i.e., a volume of space containing the body and cavity surface elements for each surface element pair is then defined. The neighborhood is defined so as to contain the body and cavity surface elements in the pair, but no other surface elements or parts of surface elements belonging to another surface element pair.

Novel body motion constraints and interference-free small incremental body motions are then developed that result in the great improvement in speed and accuracy of the present method. Body motion constraints define the possible small body motions that can be carried without interference. They are defined for every surface element pair so that the body and the cavity surface elements do not interpenetrate and the body movement does not cause the body surface element in the pair to leave the neighborhood. An incremental movement of the body that satisfies the body motion constraints along a defined preferred motion direction is then determined. The incremental body movement is guaranteed to be interference-free and brings the body further into the cavity. As a result of determining a body movement that respects the body motion constraints, an expensive body and cavity interference test at each step is avoided. Further, because the body motion is along a preferred direction, there is no need for guessing or searching for new interference-free body configurations for each step, or moving by much smaller steps that are required to move with fine resolution motion grids.

The body is then incrementally moved (or movement is simulated by the incremental motion computed in the previous step to a new configuration closer to the final inserted configuration. The steps of the method are then repeated, starting with determining surface element pairs with the new body configuration, until the body reaches its final configuration within the cavity or becomes stuck in the cavity before reaching the final configuration. Each time the process steps are repeated, an incremental body movement in the body insertion trajectory is determined.

The trajectory determined by the present method can be used by an apparatus to insert a solid body tightly fitting into a cavity without interference. It can also be used to simulate the motion of a proposed solid body and cavity shapes to determine whether it is possible to insert the body into the cavity without interference. If the proposed body gets stuck in the cavity during the insertion, the body and cavity shapes can be modified to allow the insertion to continue. The shapes can be modified until insertable, tightly fit body and cavity shapes for the final inserted configuration are obtained. Computer aided manufacturing (CAM) techniques can be employed to manufacture the solid body that has the interference-free insertion trajectory into a cavity as determined by the present method.

BRIEF DESCRIPTION OF THE DRAWINGS

FIGS. 2, 2A, 2b, and 2B.1 show a drawing of a body surface and a cavity surface and corresponding body and cavity surface elements.

FIG. 3a is a drawing of the body inside the cavity, their corresponding surfaces and surface elements, and paired surface elements.

FIG. 3b is a drawing detail of one pair of surface elements and their neighborhood.

FIGS. 5A, 5A.1, 5A.2 and 5A.3 show a drawing of the body, the cavity, their respective coordinate frames, and the body motions along the coordinate axes.

FIG. 5b is a drawing detail of a surface element pair and the interference-free configurations associated to its body motion constraints.

FIGS. 6A, 6A.1, 6A.2, 6A.3 and 6A.4 show a drawing showing a body motion, a body motion trajectory, and their approximation.

FIGS. 6B, 6B.1, 6B.2, 6B.3 and 6B.4 show a drawing detail of a small body motion and the configuration constraints associated with a surface element pair during the motion.

FIG. 7 is a drawing of an example of a body stuck in a cavity.

FIGS. 8, 8A–8D show a drawing showing an example of an interference-free extraction trajectory.

FIGS. 11, 11a, and 11b show a drawing of a body stuck in cavity and the interferences preventing further insertion of the body into the cavity.

FIGS. 12, 12a–12d show a drawing of a body stuck into a cavity, the interferences preventing further insertion of the body into the cavity, and the new cavity shape that allows the body insertion to proceed.

FIG. 14 is a block diagram of a novel apparatus used for the design and manufacturing of tightly fit insertable body and cavity shapes.

DETAILED DESCRIPTION OF THE INVENTION

This invention relates to the problem of inserting a moving solid body into a fixed cavity without encountering interferences. Given the shape of the body and the shape of the cavity, the goal is to find an interference-free insertion trajectory that takes the body from an initial configuration (position and orientation) outside the cavity to a final configuration inside the cavity. The insertion trajectory determines how to vary the position and orientation of the body in space so as to continuously move it from its initial to its final configuration without penetrating the cavity walls. (Alternatively the body could be fixed and the cavity moved or the body and cavity could move in relation to one another. These motions are also contemplated by the invention and could be implemented by one skilled in the art given this disclosure. These alternative motions are eliminated from the discussion below with no loss in generality.)

The method described below is best suited for the interference-free insertion of a solid body into a cavity with the following characteristics:

1. The body and cavity have complex 3-dimensional shapes. Complex 3-dimensional shapes typically require thousands of parameters to define them.
2. The body is tightly fit into the cavity during the insertion trajectory. A tight fit occurs when (a) the body and cavity shapes are almost complementary. (Two shapes are almost complementary when the distance between their surfaces is much smaller than their height, width, and length) and; (b) the clearance between the body and the cavity is much smaller than their height, width, and length in a substantial portion of the insertion trajectory. (A substantial portion of a trajectory is one whose length is large relative to the maximum clearance in that portion. The clearance is the maximum lateral distance that the body can move without penetrating the cavity's walls.)
3. The insertion trajectory of the body into the cavity is complex. Complex trajectories require thousands of small, incremental position and orientation motions to take a body from the starting to the final configuration.

Figure 1:
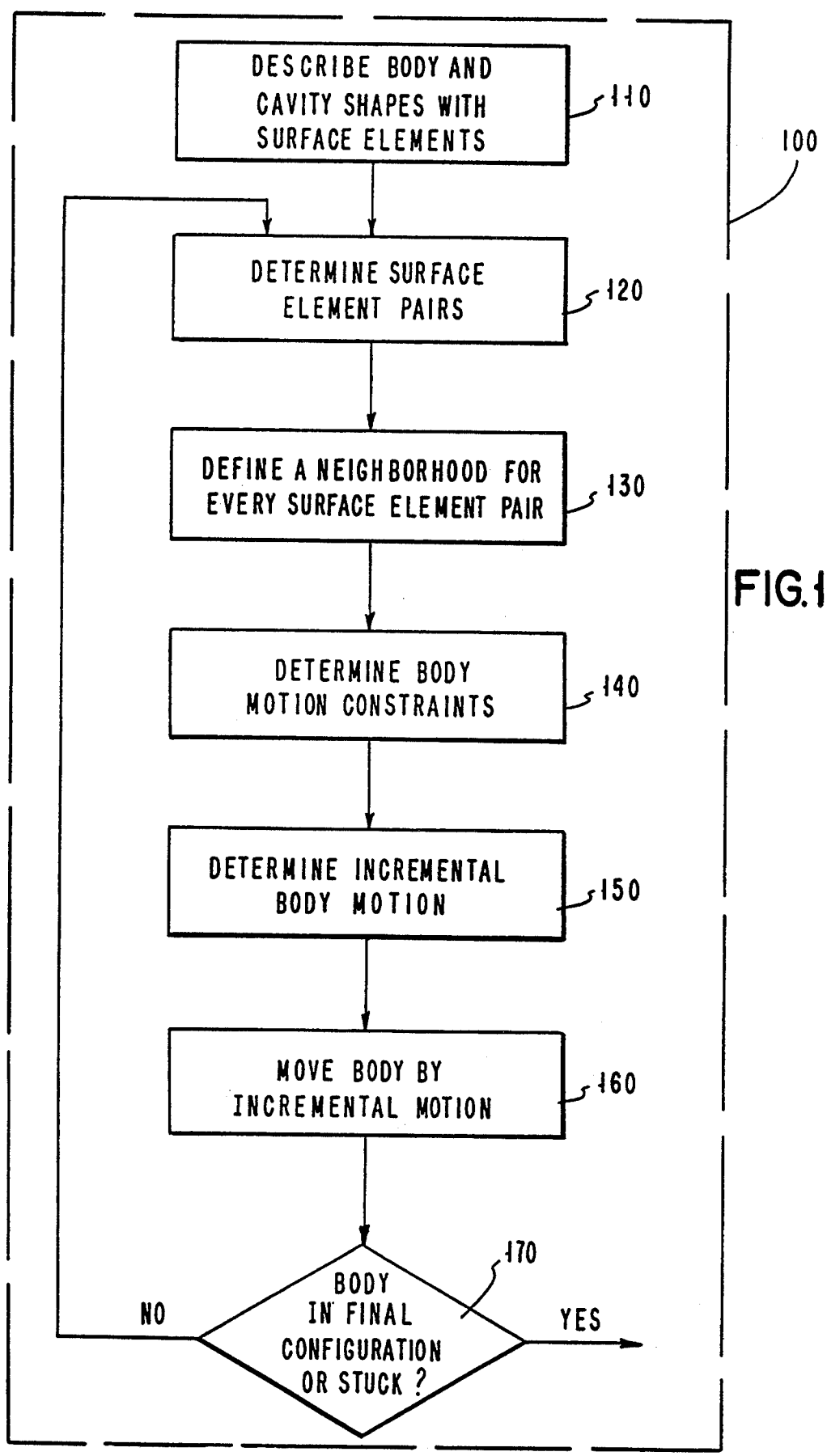
FIG. 1 is a flowchart describing the steps of the novel method for finding an interference-free trajectory of a moving solid body tightly fitting into a cavity.

FIG. 1 is a flowchart describing the main steps of the novel present method 100 for finding an interference-free trajectory of a moving solid body tightly fitting into a cavity. The method begins by first describing the body surface shape by a finite set of body surface elements and the cavity surface shape by a finite set of cavity surface elements 110. Next, a set of surface element pairs is determined 120. Each surface element pair in the set comprises a body surface element and a corresponding cavity surface element. A neighborhood is then defined for each surface element pair 130. Each neighborhood contains the body and cavity surface elements in the pair, but no other surface elements or parts of surface elements belonging to another surface element pair. Body motion constraints are developed for every surface element pair 140 so that the body and the cavity surface elements in the pair do not interpenetrate and the body movement does not cause the body surface element in the pair to leave the neighborhood. An incremental movement of the body is then determined that satisfies the body motion constraints 150. The incremental movement of the body is along a defined preferred motion direction. The body is then moved by the incremental amount to a new configuration 160. The steps in boxes 120, 130, 140, 150 and 160 are repeated 170 with the new body configuration until the final body configuration is reached or until a stuck body configuration is attained.

By constraining the body motions 140 so that no body surface element penetrates a cavity surface element, the body and cavity surfaces never interpenetrate during the small incremental body motions that define the insertion trajectory. As a result, the method does not have to perform an expensive body and cavity interference test at each step. Further, the method computes the small incremental motions necessary to insert the body into the cavity. This circumvents the need for guessing and searching for new interference-free body configurations for each step. Further, the incremental movement 150 is only limited by the body motion constraints 140 and not by the very small motions that are required to move with fine resolution motion grids. The clearance and the neighborhood allow incremental motions that are significantly larger than those allowed in fine resolution motion grids. This significantly reduces the number of small incremental movement steps 150 necessary to insert the body into the cavity. The advantages of the present method significantly decrease the time needed to obtain the interference-free trajectory and enable solutions to problems with characteristics of complex shapes, tight fit, complex insertion trajectory.

The method 100 of FIG. 1 starts by describing the body and cavity shapes with surface elements 110. The input to the method is a solid body described by a body surface shape and a cavity described by a cavity surface shape. The surface shapes can be described by one or more surface primitives, such as planar facets, spline surfaces, Bezier cubic patches, or any other known surface primitive. These are typically available in Computer-Aided Design (CAD) systems where the shapes are designed. The method step 110 produces a body and cavity shape description with surface elements. FIG. 2 shows an example of the solid body 200 defined by its body surface shape 210 and a cavity 250 defined by its cavity surface shape 230. The body surface shape 210 is further described by body surface elements 220. The cavity surface shape 230 is further described by cavity surface elements 240. The surface elements can be points, planar facets, or spline patches. One skilled in the art could readily come up with a number of known techniques for defining the body shape 210 and the cavity shape 230 with a finite set of surface elements 220 and 240 to within prespecified tolerances. (Note that body surface and cavity surface elements can be defined using the same techniques.) Surface subdivision and meshing techniques, such as commonly used in Computer Graphics and Finite Element Methods (FEM), can be used to produce the set of surface elements. See *Curves and Surfaces for Computer-Aided Geometric Design: A Practical Guide*, by G. Farin, Academic Press, 1988 for various ways to produce sets of surface elements. This reference is herein incorporated by reference.

In one preferred embodiment, the body surface elements 220 are points 228 and the cavity surface elements 240 are planar facets 249. The body points 228 are obtained by sampling the body surface shape 210 for surface points (typically 228) at regular intervals forming a grid (typically 225) that covers the body surface shape 210 in its entirety. The cavity planar facets 249 are obtained by sampling the cavity surface shape 230 for cavity surface points 247 and normal surface vectors 248 at regular intervals forming a grid (typically 235) that covers the cavity shape 230 in its entirety. The cavity surface point 247 and cavity surface normal vector 248 define the cavity planar facet 249. Again, surface descriptions like this are well known and one with ordinary skill in the art would know many equivalent ways of describing the body surface 210 and cavity surface 230 with surface elements. These equivalent descriptions are within the contemplation of the present invention.

FIGS. 3a and 3b illustrate the step 120 of method 100 shown in FIG. 1, i.e., the pairing of body surface elements 320 and cavity 370 surface elements. Referring to FIG. 3a, this step determines surface element pairs such as pairs 341, 342, and 343 of body surface 310 and cavity surface 360. A detail of a typical surface element pair 340 is shown in FIG. 3b. The surface element pair 340 consists of a body surface element 320 of body surface 310 and a cavity surface element 370 of cavity surface 360. The body and cavity surface elements are paired such that the distance between the body surface element of the pair and the cavity element of the pair is smaller than the distance between the body element of the pair and any other cavity element. The pairing is established by computing the distances between each body surface element at the body configuration and each cavity surface element and then choosing the pairs whose distance is minimum. In one preferred embodiment, the distance between body surface points and cavity planar facets is easily computed as the distance between a point and a planar facet. Other equivalent methods of pairing the closest body and cavity surface elements are within the contemplation of the invention.

The third step 130 of the method 100 of FIG. 1 defines a neighborhood for every surface element pair. The neighborhood of a surface element pair is a portion of space containing the body surface element and the cavity surface element, and no other surface elements or parts of surface elements belonging to another surface element pair. Examples of neighborhoods are spheres and polyhedral volumes. The neighborhoods are directly computed from the type and dimensions of the body and cavity surface elements. FIG. 3b shows a neighborhood 390 for the surface element pair 340 defined by body surface element 320 and cavity surface element 370. The neighborhood 390 is a sphere containing body surface element 320 and cavity surface element 370.

Figure 4B:
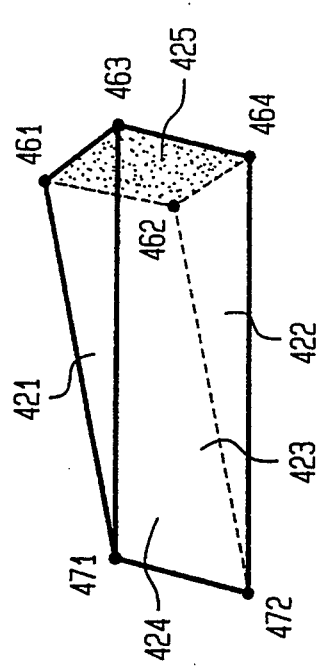
FIG. 4b is a drawing detail of the structure of a pie-slice shaped volume neighborhood.
Figure 4A:
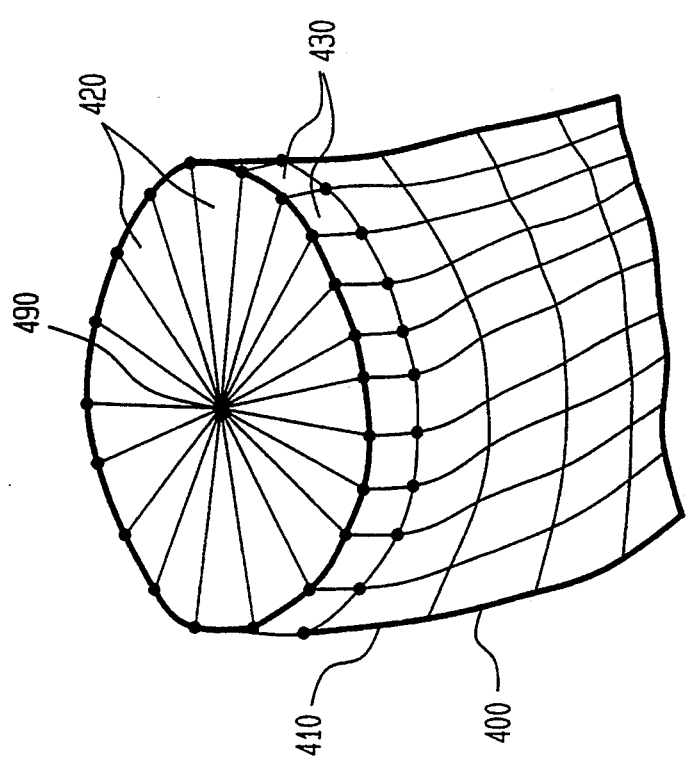
FIG. 4a is a drawing of a preferred neighborhood embodiment comprising pie-slice shaped volumes constructed from the planar facet cavity surface elements.

FIG. 4 illustrates a preferred embodiment 400 in which neighborhoods (FIG. 4a) are pie-slice shaped volumes 420 whose walls are planar facets defined by cavity surface elements 430. See FIG. 4b. Each pie-slice neighborhood 420 is defined by five planar faces: top 421, bottom 422, right 423, left 424 and cavity planar facet 425. The pie-slice is defined by the four points 461, 462, 463, 464 on the cavity planar facet 425 and two points 471 and 472 on the main cavity axis 490.

The next step 140 of the method 100 of FIG. 1 determines body motion constraints for every surface element pair so that the body and the cavity surface elements do not interpenetrate and the body movement does not cause the body surface element in the pair to leave the neighborhood 140. The body motion constraints define the set of body configurations in which the body does not penetrate the cavity.

The body motion constraints are formulated as follows. Refer to FIG. 5a. First, the body 500 is associated with a body coordinate frame 520 with origin 521 and the cavity 550 is associated with a cavity coordinate frame 570 with origin 571. The cavity coordinate frame 570 is fixed, while the body coordinate 520 frame moves with the body. The configuration (position and orientation) of the moving body 500 with respect to the cavity 550 is described with six configuration parameters corresponding to three translations, 511, 512, and 513, denoted by the 3-dimensional vector $\bar{p}$ and three rotations, 514, 515, and 516, denoted by the 3-dimensional vector $\bar{\theta}$ of the body along the cavity's coordinate frame axes 572, 573, and 574.

The location of a given point 530 on the body surface 510 relative to the origin of the body coordinate frame 521 is described is denoted by the 3-dimensional vector $\bar{b}$. The position of this same point with respect to the origin of the cavity coordinate frame 571 is denoted by the 3-dimensional vector $\bar{v}$.

The position $\bar{v}$ denotes the location of the body point $\bar{b}$ when the body is oriented by $\bar{\theta}$ and translated by $\bar{p}$ with respect to the cavity coordinate frame 570. The body is oriented by successively rotating it around coordinate axes 572, 573, and 574 and then translating it along the same axes. To orient the body point the standard $3 \times 3$ rotation matrix $Rot(\bar{\theta})$ is used to specify the orientation of the body with respect to the cavity's coordinate frame. $F(\bar{p}, \bar{\theta})$ denotes this transformation of mapping points in body coordinates to points in cavity coordinates in position $\bar{p}$ and orientation $\bar{\theta}$:

$$\bar{v} = F(\bar{p}, \bar{\theta}) \cdot \bar{b} = Rot(\bar{\theta}) \cdot \bar{b} + \bar{p}$$

In this representation, the position $\bar{v}$ of the body point $\bar{b}$ is computed by first forming the dot product of the rotation matrix $Rot(\bar{\theta})$, corresponding to the orientation $\bar{\theta}$ of the body with respect to the cavity, and the displacement $\bar{b}$ of the body point with respect to the body and then adding the displacement $\bar{p}$ of the body with respect to the cavity.

Let H be the function describing the cavity surface shape 560. A point $\bar{x}$ lies on or inside the cavity when the function computed at the point is equal to zero or negative, respectively:

$$H(\bar{x}) \leq 0$$

In particular, a body point $\bar{b}$ in configuration $(\bar{p}, \bar{\theta})$ lies on or inside the cavity when the function computed at the point, is equal to zero or negative, respectively:

$$H(F(\bar{p}, \bar{\theta}) \cdot \bar{b}) \leq 0$$

Note that the body configuration includes both the position and orientation of the body.

The above condition, formulated over the set of all body points $\bar{b}$, defines the body configuration constraints which must hold for the body not to penetrate the cavity surface.

The set of body configurations for which the body and the cavity do not interpenetrate is defined as the set of positions and orientations for which all the points in the body lie on or inside the cavity surface. This set of configurations is called the body configuration space $\Gamma$:

$$\Gamma = \{(\bar{p}, \bar{\theta}) | H(F(\bar{p}, \bar{\theta}) \cdot \bar{b}) \leq 0, \forall \bar{b} \in B\}$$

In this representation $\bar{b}$ is the set of all points that define the body surface, B, $(\bar{p}, \bar{\theta})$ is the body configuration, $F(\bar{p}, \bar{\theta}) \cdot \bar{b}$ is the position of body point $\bar{b}$ with respect to the fixed cavity coordinate frame, and H is the function that describes the cavity surface 560.

Pursuing the formulation of the body motion constraints, the finite set of surface elements describing the body and cavity are used. (See the discussion of step 110 of method 100 in FIG. 1.) The cavity surface shape $H(\bar{x})$ 560 is described by a finite set of cavity surface elements 580 denoted by $h_i(\bar{x})$. The body surface shape 510 is described by a finite set of body surface points 540 denoted by $b_j$.

Thus, the configuration constraints, defining the non-interference body positions and orientations, can be represented more simply by accounting only for selected points on the body surface, i.e., the set of body surface points 540. The representation can be reformulated only for the specific set of points, $\bar{b}_j$, that, in one preferred embodiment, are the set of points chosen in step 110 to describe the body. As before, this set of points in all configurations must lie on or inside the cavity:

$$H(F(\bar{p}, \bar{\theta}) \cdot \bar{b}_j) \leq 0$$

Because of the tight fit between the body and the cavity, a motion of each body surface point 540, $\bar{b}_j$, is constrained by a cavity surface element 580 in its immediate neighborhood. That cavity surface element 580 imposes configuration constraints that subsume the configuration constraints imposed by all other cavity surface elements, provided the body surface point remains in the neighborhood associated with the surface element pair. For each body configuration in the insertion trajectory, it is sufficient only to consider the configuration constraints imposed by the cavity surface elements that are closest to each body surface point. The configuration constraint corresponding to a surface element pair can then be formulated as the condition for which the body surface point in the pair lies on or inside the cavity surface element in the defined neighborhood.

Referring to FIG. 5b, for each surface element pair 590 as determined in step 120 of method 100 and its associated neighborhood 591 as determined in step 130 of method 100, the body motion constraint specifying that the body surface point 592 denoted by $b_j$ in configuration $(\bar{p}, \bar{\theta})$ lies on or inside cavity surface element 593 denoted by $h_i$ while the body surface point stays inside the neighborhood 591 denoted by $\Delta_{ij}$.

$$h_i(F(\bar{p}, \bar{\theta}) \cdot \bar{b}_j) \leq 0 \text{ for } (F(\bar{p}, \bar{\theta}) \cdot \bar{b}_j) \in \Delta_{ij}$$

In this representation, $\Delta_{ij}$ is the set of points in the volume defining the neighborhood of body surface element $b_j$ and cavity surface element $h_i$. The inequality limits each body surface point to the portion of the neighborhood that is on or within the cavity surface element. This constraint defines the local configuration constraint of the surface element pair. ("Local" limits the constraint to a single surface element pair of the set of pairs.) The shaded region 595 illustrates this constraint.

In one preferred embodiment, the cavity surface element pair is a planar facet and the neighborhood is a pie-sliced shape volume. The cavity surface element $h_i$ is described as a planar facet by a plane:

$$h_i(\bar{x}) = \bar{a}_i \cdot \bar{x} - c_i = 0$$

(this is a standard vector representation of a plane.) The pie-sliced shape neighborhood $\Delta_{ij}$ is described by five planar facets, as illustrated in FIG. 4b, 421, 422, 423, 424, and 425. The five planar facets are described by five intersecting planes, in the standard form:

$$A_i \bar{x} - C_i = 0$$

In this representation, $A_i$ is the 3×5 matrix defining the planes and $C_i$ is the 5-dimensional vector defining their displacement.

The local configuration constraint specifying that a body surface point $\bar{b}_j$ at configuration $(\bar{p}, \bar{\theta})$ lies on or inside the neighborhood $\Delta_{ij}$ defined by cavity surface element $h_i$ is then:

$$A_i \cdot (F(\bar{p}, \bar{\theta}) \cdot \bar{b}_j) - C_i \leq 0$$

for neighborhood $\Delta_{ij}$. This means that a given body point cannot leave the neighborhood or penetrate the cavity planar facet defining the neighborhood.

The next step of method 100 is determining an incremental movement of the body 150. The body movement should be along a defined preferred motion direction and should satisfy the body motion constraints defined in by step 140.

Referring to FIG. 6a, a continuous body motion 600, denoted T(t) specifies the position and orientation of the body at time t. A body trajectory traj(T(t)) 610 is the set of body configurations reached during a body motion from the starting configuration 620 to the ending configuration 630. The body trajectory is the locus of body configurations 670 (position and orientation) of the continuous body motion 600. A body insertion motion is a body motion that takes the body from an initial configuration outside the cavity 620 to a final configuration inside the cavity 630. A body insertion motion is interference-free when the body does not penetrate the cavity at any time during the motion. In an interference-free body insertion trajectory, all body configurations in trajectory must satisfy the configuration constraints. For all positions $\bar{p}(t)$ and orientations $\bar{\theta}(t)$ along the motion T(t), all the body points $\bar{b}$ in the trajectory configurations must lie on or inside the cavity surface:

$$traj(T(t)) = \{T(t) = (\bar{p}(t), \bar{\theta}(t)) | H(F(\bar{p}(t), \bar{\theta}(t)) \cdot \bar{b}) \leq 0, \forall \bar{b} \in B, t \in [t_0, t_f]\}$$

The configuration $T(t_0) = (\bar{p}_0, \bar{\theta}_0)$ is the initial body configuration 620 at starting time $t_0$ and the configuration $T(t_f) = (\bar{p}_f, \bar{\theta}_f)$ is the final configuration 630 at ending time $t_f$.

In general, determining the exact body motion 600 is only possible when the shapes are simple, the motions are simple, or the body has 2 or 3 degrees of freedom. It is very difficult for complex shapes and complex trajectories, as is the case here. Instead, an approximation of the body insertion motion 650 is determined comprising many small, incremental motions 660 describing small rotations and translations of the body, denoted $(\bar{\epsilon}_k, \bar{a}_k)$.

These small motions determine the locus of body configurations 670 in the insertion trajectory, denoted $(\bar{p}_k, \bar{\theta}_k)$. A motion $(\bar{\epsilon}_k, \bar{a}_k)$ is small when it does not exceed prespecified amounts:

$$|\bar{\epsilon}_k| \leq \bar{\epsilon}_{max}$$

$$|\bar{a}_k| \leq \bar{a}_{max}$$

The small incremental motions define a sequence of body configurations 670 in the body insertion trajectory 650 that approximate the insertion trajectory 610. The body configurations 670 are successively determined from the small incremental motions 660 by the relation:

$$(\bar{p}_{k+1}, \bar{\theta}_{k+1}) = F(\bar{\epsilon}_k, \bar{a}_k) \cdot (\bar{p}_k, \bar{\theta}_k)$$

In this representation, the configuration $(\bar{p}_k, \bar{\theta}_k)$ at setp k is composed with the kth small incremental motion $(\bar{\epsilon}_k, \bar{a}_k)$ by means of the operator F and the dot product to determine the next $k+1$ $(\bar{p}_{k+1}, \bar{\theta}_{k+1})$ configuration.

The approximate body insertion trajectory 650, denoted traj(T(k)), is then a sequence of m body configurations 670 such that the starting body configuration 671 is $T(0) = (\bar{p}_0, \bar{\theta}_0)$ and the final body configuration 672 is $T(m) = (\bar{p}_m, \bar{\theta}_m)$. The trajectory is interference-free when all the body configurations are interference-free:

$$traj(T(k)) = \{T(k) = (\bar{p}_k, \bar{\theta}_k) | h_i(F(\bar{p}_k, \bar{\theta}_k) \cdot \bar{b}_j) \leq 0, \forall \bar{b} \in B, 0 \leq k \leq m\}$$

The problem of finding an interference-free body insertion trajectory is therefore reduced to finding a sequence of small body movements $(\bar{\epsilon}_k, \bar{a}_k)$ which satisfy the configuration constraints and do not exceed a predefined maximum motion, i.e., the largest motion that does not cause the body surface points to penetrate the cavity surface elements in the surface element pairs or go out of their neighborhoods.

Refer to FIG. 6b which shows a preferred way to determine small body movements 665. Recall that step 140 of method 100 in FIG. 1 determined body motion constraints for every surface element pair so that: 1. the body and the cavity do not interpenetrate and 2. the body movement does not cause the body surface element in the pair to leave the neighborhood. Neighborhoods provide a natural bound for the incremental body motions. However, while the body motion constraints describe the set of interference-free body configurations, they do not indicate how should the body move to get closer to the final inserted position.

The distance between the current body configuration and the final body configuration is shortened with a preferred motion direction. Essentially, the preferred motion direction is implied in the problem as the direction that inserts the body into the cavity. The preferred motion direction, together with the body motion constraints, show how to move the body closer to the final inserted configuration without interference. For example, the preferred insertion direction 690 of the body in FIG. 6a is downwards, i.e., inward into the cavity. The preferred motion direction can be defined as a function, denoted $\tau$, of the body motion parameters $(\bar{\epsilon}, \bar{a})$.

Having chosen a preferred motion direction 690, the largest body motion is found in that direction 690 that satisfies the body motion constraints for all the surface element pairs and their corresponding neighborhoods.

This incremental body motion step is guaranteed to bring the body closer to its final inserted configuration and is interference-free. Finding the largest incremental motion (and not just any incremental motion) reduces the number of small motion steps necessary to take the body from its starting to its ending configuration in the fewest possible steps.

The optimization of the preferred motion direction function subject to the body motion constraints yields the maximum body motion displacement. An optimization problem is formulated where the objective function is the preferred motion direction function $\tau(\bar{\epsilon}, \bar{\alpha})$ and the constraints are: 1. the body motion constraints $h_i(F(\bar{p}, \bar{\theta}) \cdot \bar{b}_j) \leq 0$, 2. the neighborhood condition $(F(\bar{p}, \bar{\theta}) \cdot \bar{b}_j) \in \Delta_{ij}$, and 3. the small motion constraints $|\bar{\epsilon}_k| \leq \bar{\epsilon}_{max}$ and $|\bar{\alpha}_k| \leq \bar{\alpha}_{max}$.

The optimization problem is then:

Maximize $\tau(\bar{\epsilon}_k, \bar{\alpha}_k)$ subject to $$h_i(F(\bar{p}_k, \bar{\theta}_k) \cdot \bar{b}_j) \leq 0$$

and $$(F(\bar{p}_k, \bar{\theta}_k) \cdot \bar{b}_j) \in \Delta_{ij}$$

and $$|\bar{\epsilon}_k| \leq \bar{\epsilon}_{max}$$

$$|\bar{\alpha}_k| \leq \bar{\alpha}_{max}$$

These representations state that the largest incremental movement within the neighborhood in the preferred motion direction (here, into the cavity or down) is constrained so that 1. the body surface (selected points on the body surface) does not penetrate the cavity surface and 2. each body surface point does not leave its respective neighborhood.

The additional limits on translation and rotational movement are imposed to limit the motion error due to approximation, i.e., the amount each incremental body motion 660 can deviate from the exact body motion 610 in the exact insertion trajectory. The resulting problem is a general non-linear optimization problem.

The non-linear optimization problem is, in general, difficult to solve. In one preferred embodiment, the above non-linear optimization problem is transformed into a linear programming problem.

The formulation of the linear optimization problem is described for step $k+1$ (a next iteration of the method steps, box 170 of FIG. 1) using the result of step k. First, $\bar{v}_{jk}$ is described, as the staring position of body surface points $b_j$ in configuration $(\bar{p}_k, \bar{\theta}_k)$:

$$\bar{v}_{jk} = F(\bar{p}_k, \bar{\theta}_k) \cdot \bar{b}_j$$

The new position $\bar{v}_{jk+1}$ of body surface point $b_j$ in configuration $(\bar{p}_{k+1}, \bar{\theta}_{k+1})$ is obtained by moving $b_j$ in configuration $(\bar{p}_k, \bar{\theta}_k)$ by $(\bar{\epsilon}_k, \bar{\alpha}_k)$:

$$\bar{v}_{jk+1} = F(\bar{\epsilon}_k, \bar{\alpha}_k) \cdot \bar{v}_{jk} = Rot(\bar{\alpha}_k) \cdot \bar{v}_{jk} + \bar{\epsilon}_k$$

Since $(\bar{\epsilon}_k, \bar{\alpha}_k)$ is a small motion, it can be approximated by the linear form:

$$\bar{v}_{jk+1} \simeq (\bar{\alpha}_k \times \bar{v}_{jk}) + \bar{v}_{jk} + \bar{\epsilon}_k$$

for $|\bar{\epsilon}_k| \leq \epsilon_{max}$ and $|\bar{\alpha}_k| \leq \bar{\alpha}_{max}$.

The local configuration constraints are then written as:

$$h_i(\bar{v}_{jk+1}) \leq 0$$

$$h_i((\bar{\alpha}_k \times \bar{v}_{jk}) + \bar{v}_{jk} + \bar{\epsilon}_k) \leq 0$$

In one preferred embodiment, the cavity surface element $h_i(\bar{x})$ is a planar facet and the neighborhood a pie-sliced volume defined by five intersecting planes $A_i \cdot \bar{x} - C_i = 0$. Substituting above, the local configuration constraints become linear:

$$A_i((\bar{\alpha}_k \times \bar{v}_{jk}) + \bar{v}_{jk} + \bar{\epsilon}_k) - C_i \leq 0$$

$$(\bar{v}_{jk} \times A_i) \cdot \bar{\alpha}_k + (A_i \cdot \bar{\epsilon}_k) \leq C_i - A_i \cdot \bar{v}_{jk}$$

Finally, a linear preferred direction function $\tau(\bar{\epsilon}_k, \bar{\alpha}_k)$ is picked to make the optimization function linear. Since a clear preferred insertion direction is a downward motion 690 along the cavity's vertical axis z, set $\tau(\bar{\epsilon}_k, \bar{\alpha}_k) = -\epsilon_{zk}$.

The resulting linear optimization problem is then:

Maximize $-\epsilon_{zk}$

Such that $$(\bar{v}_{jk} \times A_i) \cdot \bar{\alpha}_k + (A_i \cdot \bar{\epsilon}_k) \leq C_i - A_i \cdot \bar{v}_{jk}$$

$$|\bar{\epsilon}_k| \leq \bar{\epsilon}_{max}$$

$$|\bar{\alpha}_k| \leq \bar{\alpha}_{max}$$

This linear optimization problem can be solved with standard linear optimization techniques for very large problems involving thousands of constraints, as is the case of the complex tightly fit shapes that are the subject of this invention.

An alternative embodiment is to choose a quadratic preferred motion direction function, one that minimizes rotations while maximizing the vertical downward motion. The problem becomes a quadratic linear programming problem and is amenable to solution with standard quadratic linear programming methods, such as those based on non-negative least-square (NNLS) methods.

The sixth step 160 of the method 100 in FIG. 1 comprises moving the body from the current configuration to the next configuration by the incremental body movement computed in the previous step. The next configuration of each body surface element is directly obtained from the current configuration of the body element and the incremental body movement:

$$(\bar{p}_{k+1}, \bar{\theta}_{k+1}) = F(\bar{\epsilon}_k, \bar{\alpha}_k) \cdot (\bar{p}_k, \bar{\theta}_k)$$

Steps 120 to 160 of method 100 in FIG. 1 are repeated 170 until a final body configuration is reached or the body is stuck. Reaching the final configuration is tested by comparing the current body configuration 670 and the desired final body configuration 672. The body is stuck when the incremental body movement in the preferred motion direction, as computed in the previous step, is zero. FIG. 7 shows an example of such stuck configuration: body 700 cannot move any further towards the bottom of cavity 750. If the body has reached the final configuration, or is stuck, the method ends (the "yes" branch of box 170 of FIG. 1.) If not, the method is iterated again starting at box 120 (the "no" branch of box 170).

The method 100 of FIG. 1 computes an interference-free body insertion trajectory into a cavity. The successive incremental motions in the insertion trajectory bring the body closer and closer to its final configuration inside the cavity. The insertion trajectory is thus monotonically decreasing with respect to the preferred body insertion trajectory. When no progress can be made, the body is stuck because no motion in the preferred motion direction is possible.

There are many applications and embodiments of the present method contemplated by the inventors. Some of them are described below.

It should be noted that, although we describe this method in the context of insertion of a body into a cavity, it should be noted that it is equally applicable to extraction of a body from a cavity, or motion of a body within a cavity, depending on the choice of initial and final configurations and preferred motion direction.

The method 100 of FIG. 1 can easily be adapted to solve the interference-free extraction trajectory problem. FIG. 8 shows an example of such an interference-free extraction trajectory. Given an initial body configuration inside the cavity 820 and a desired final body configuration outside the cavity 830, an interference-free body extraction trajectory 810 is one that takes the body from its initial configuration inside the cavity to its final configuration outside the cavity without interferences. To solve this problem, we apply the method 100, with the initial configuration 820, final configuration 830, and the preferred motion direction aimed from the initial configuration 820 towards final configuration 830 along approximate trajectory 850. It should be noted that the solution to this extraction problem can be used to determine a feasible insertion trajectory by reversing the incremental motion steps 860.

The method 100 of FIG. 1 can also be adapted easily to account for slightly compressible bodies and cavities. The compressibility is accounted for by allowing the body and cavity shapes to interpenetrate by a small pre-specified amount. Small amounts of interpenetration are permitted by allowing small amounts of interpenetration in each surface element pair. This is done by relaxing the local configuration constraints for each surface element pair allowing the body surface element to be inside the cavity surface element by a small interpenetration amount, $\Psi$. The local configuration constraints then become:

$$h_i(F(\bar{p}, \bar{\theta}) \cdot \bar{b}_j) \leq \Psi \text{ for } (F(\bar{p}, \bar{\theta}) \cdot \bar{b}_j) \Delta_{ij}$$

Setting $\Psi$ to 0 yields the original rigid body scenario. Note that all the mathematical characteristics of the optimization problem, and in particular the linearity of the optimization problem, are preserved.

The method 100 of FIG. 1 can also be easily adapted to account for user defined constraints and requirements on the characteristics of the body insertion motion. Such constraints guarantee a smooth insertion trajectory by avoiding sharp rotations in the incremental motion steps, trajectories in which the body does not exceed a predefined inclination, etc. The constraints apply to the body motion parameters $(\bar{p}, \bar{\theta})$ and can be added to the body motion constraints in the optimization problem.

Figure 9:
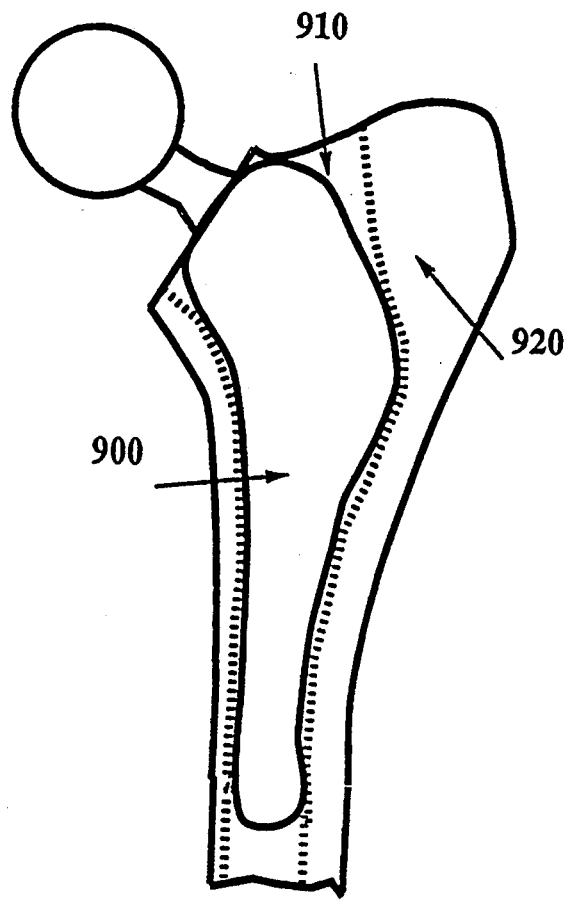
FIG. 9 is a drawing of an orthopaedic implant inserted into a cavity carved into a bone.

The method 100 of FIG. 1 is especially useful for determining the insertability of a prosthetic implant into a cavity carved in an anatomical structure, such as a bone, during reconstructive surgery. FIG. 9 shows an implant 900 inserted into a cavity 910 carved into a bone 920.

Next, a novel method is described for the design and modification of tightly fit insertable body and cavity shapes. Starting with nominal body and cavity shapes, the method modifies the body and cavity shapes so that the body can be inserted without interference into the cavity, maintaining a tight fit. The method determines both the modified body and cavity shapes and the interference-free body insertion trajectory.

Figure 10:
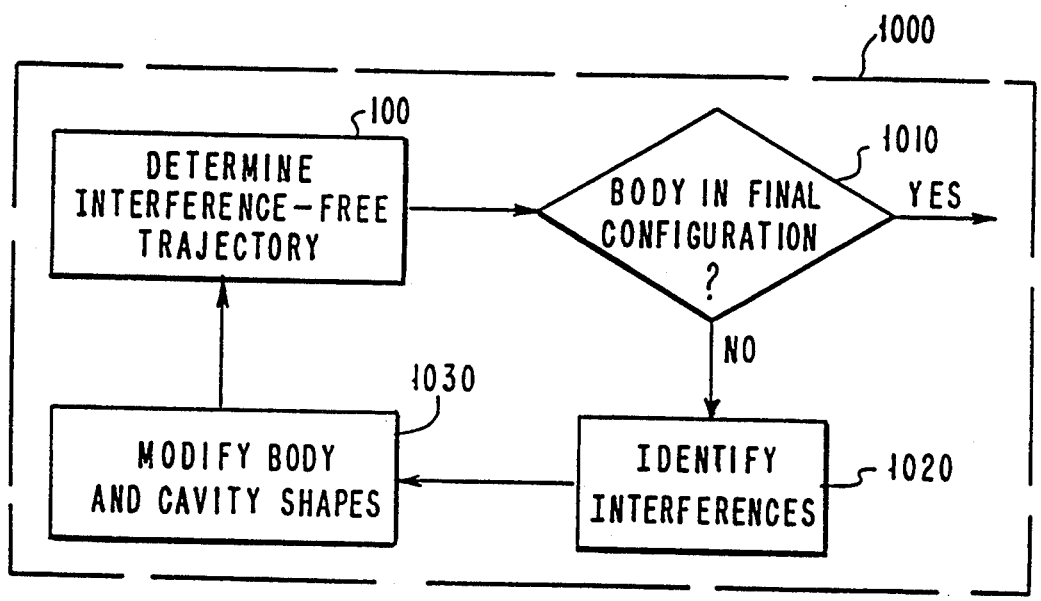
FIG. 10 is a flowchart describing the main steps of a novel method for designing and modifying tightly fit insertable body and cavity shapes and determining an interference-free body insertion trajectory.

FIG. 10 is a flowchart describing the main steps of the novel present method 1000 for designing and modifying tightly fit insertable body and cavity shapes and determining an interference-free body insertion trajectory. The method begins with two nominal body and cavity shapes and determines with method 100 previously described an interference-free body insertion trajectory. If the body is stuck before reaching its final configuration inside the cavity, the method proceeds to modify the body and cavity shapes 1010. The method first identifies the interferences between the body and the cavity that prevent the body from continuing on its insertion trajectory 1020. The interferences are caused by contacts between one or more body and cavity surface elements. The method then identifies which shape surface elements must be modified in order to proceed with the insertion, and modifies the body and cavity shapes accordingly 1030. The shape modifications guarantee that the body can always continue its insertion trajectory for at least a small amount. All steps are repeated until the body reaches its final configuration inside the cavity. The method produces new body and cavity shapes and the an interference-free body insertion trajectory for the modified shapes.

The method can be used to design body and cavity shapes by starting with a shape template from which a body shape and a complementary cavity shape are determined. The successive steps of the method will modify the body and cavity shapes as necessary. The method can be used to modify predetermined body and cavity shapes by going through the steps of the method. Note that the method produces one of many possible body and cavity shape modifications that guarantee interference-free body insertion. Having identified the surface interferences in step 1020, a choice of various shape modifications is typically available. To remove the interference, part of the body shape causing the interference can be reduced, part of the cavity shape causing the interference can be enlarged, or both actions can be taken. Further, several shape modification possibilities can be chosen, such as shortening the body or shrinking it, elongating the cavity or enlarging it. The choice can be dictated by the human designer or can automatically be made by the method based on diverse shape design and modification criteria.

The novelty of method 1000 is the automation which includes the automatic identifying of stuck body configurations, identifying the interferences causing them, identifying the parts of the body and cavity surface shapes causing interferences, and modifying these parts to allow the continuation of the body insertion. The method enables identification and visualization of interference and stuck configurations that are extremely difficult to analyze when the shapes are complex and the fit is tight. The method 1000 reduces the time and error involved in this analysis.

The method 1000 of FIG. 10 starts by determining an interference-free body insertion trajectory 100 from the given nominal body and cavity shapes. Method 100 of FIG. 1 was described in detail previously. The method 1000 then checks if the body has reached its final configuration 1010. Step 1010 of method 1000 in FIG. 10 is identical to step 170 of method 100 in FIG. 1. If the body has reached its final configuration, no further shape modifications are necessary, and the computed insertion trajectory is interference-free. If the body is stuck before reaching its final inserted configuration, the method proceeds to steps 1020 and 1030.

Figure 11:
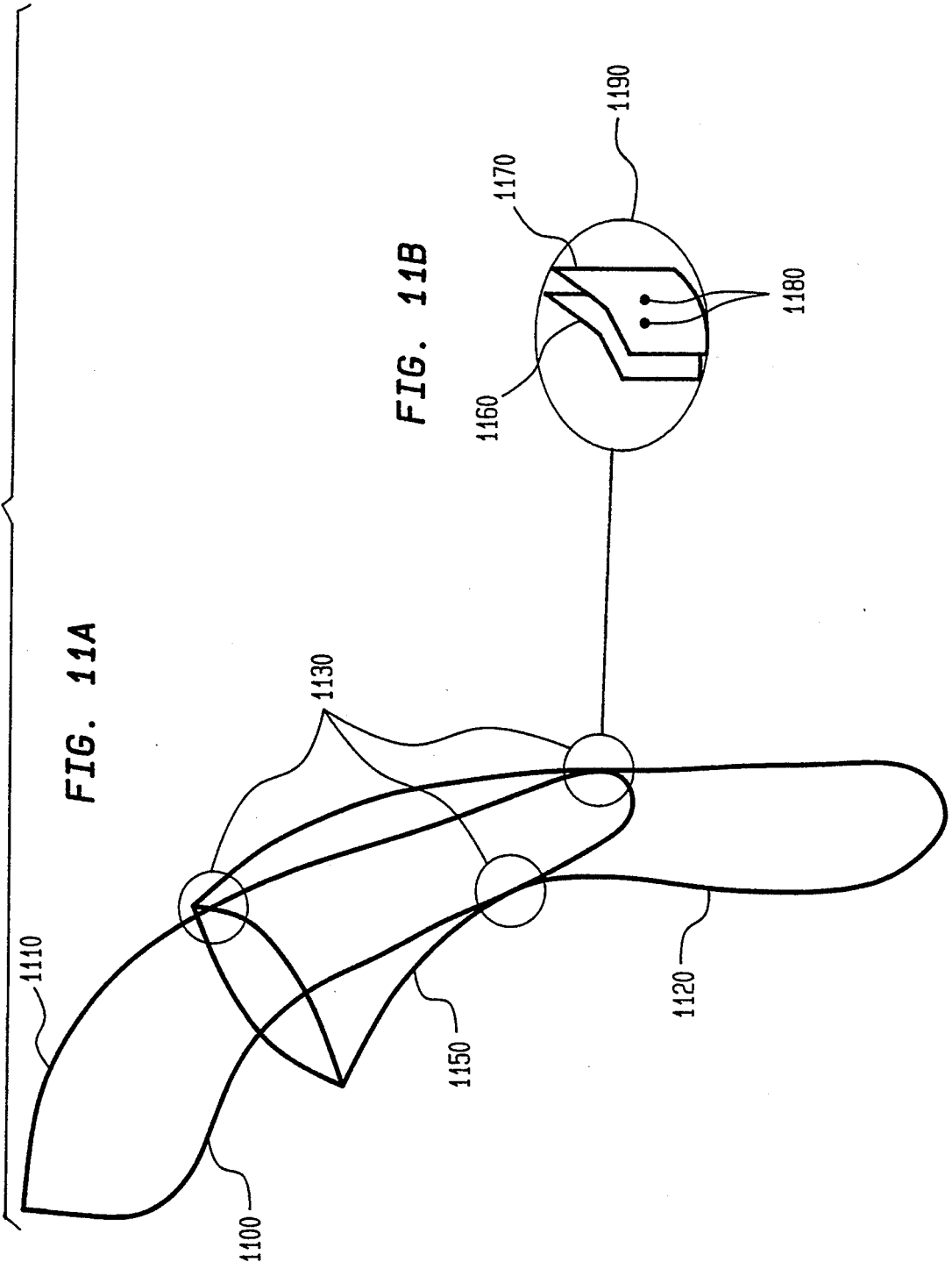

Step 1020 of method 1000 in FIG. 10 identifies the body and cavity shape interferences that prevent the body from being further inserted into the cavity. FIG. 11 shows the body 1100 stuck in cavity 1150. The interferences 1130 occur when parts of the body surface 1110 are in contact with parts of the cavity surface 1120 in such a way that no further body insertion motion is possible. When the shapes are described by surface element pairs as described in step 110 of method 100 in FIG. 1, and paired as surface element pairs as described in step 120 of method 100 in FIG. 1, each interference occurs between a body surface element 1160 and a cavity surface element 1170 in surface element pair 1180.

To determine interferences, all the surface element pairs in which the body surface element 1160 and the cavity surface element 1170 are in contact in the given configuration are found. Two surface elements are in contact when the distance between them is zero. This contact can be determined by directly measuring the distance between the body and cavity surface element pairs in the stuck configuration and selecting those pairs whose distance is zero. Contacts 1130 can also be determined by identifying the active body configuration constraints when the last incremental body movement in step 150 of method 100 in FIG. 1 was computed. A constraint is said be active when the function $h_i$ describing the cavity surface element 1170 for the body surface point $\bar{b}_j$ 1160 in body configuration $(\bar{p}_k, \bar{\theta}_k)$ is zero:

$$h_i(F(\bar{p}_k, \bar{\theta}_k) \cdot \bar{b}_j) = 0$$

In one preferred embodiment, this condition can be directly obtained from the solution to the optimization problem that is solved for determining the incremental body movement.

Figure 12:
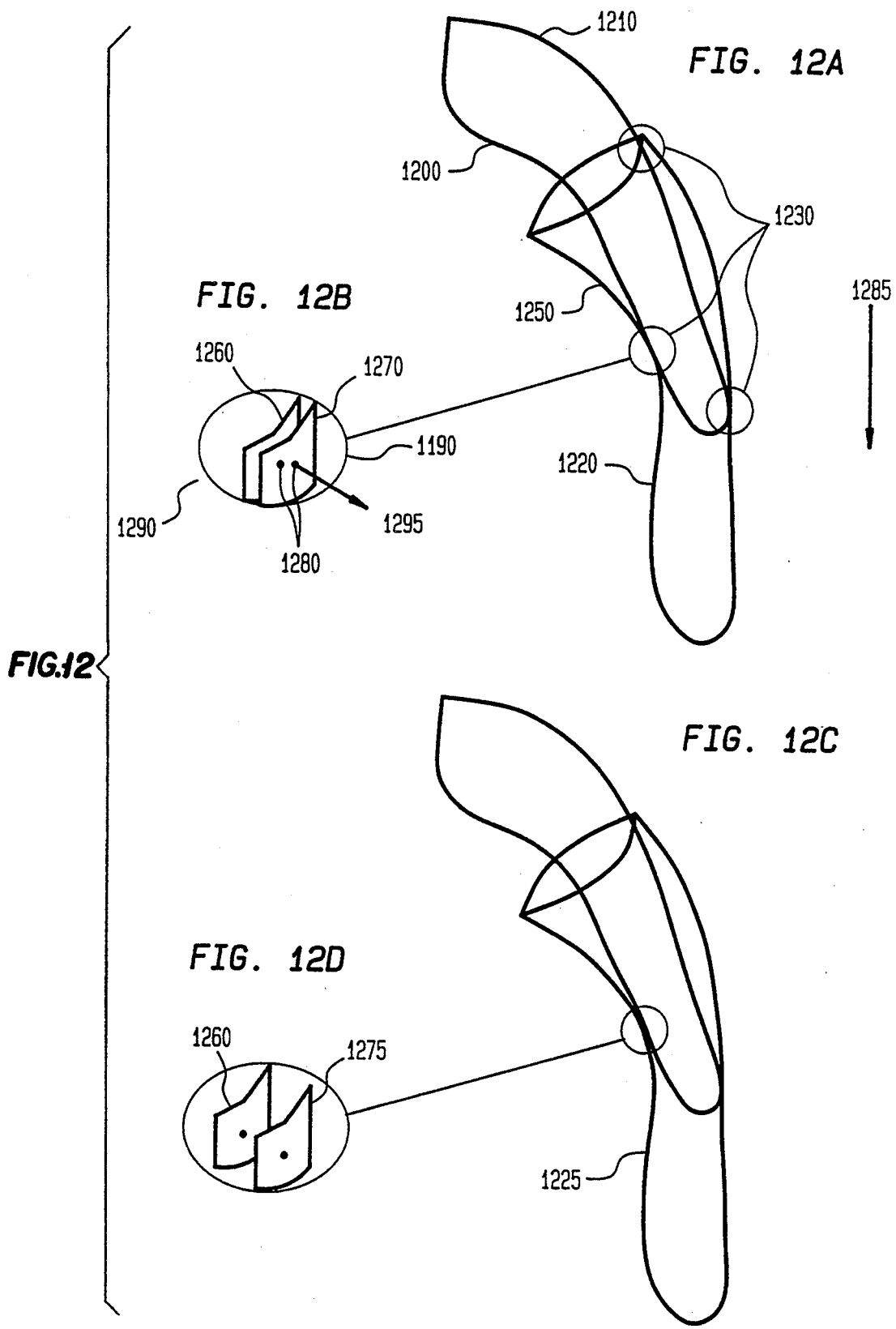

Having identified the interferences that prevent the body from being further inserted into the cavity, the next step 1030 of method 1000 in FIG. 10 modifies the body and cavity shapes to allows the further insertion of the body in the cavity. FIG. 12 shows the body 1200 stuck in cavity 1250 and their interferences 1230. One of the interferences is due to body surface element 1260 in contact with cavity surface element 1270. To remove the interference, the surface elements are moved away from each other along the vector normal to the surface at the point of contact (at the origin of vector 1295) and in the direction of the preferred motion direction 1285. Moving the surface element away amounts to modifying the body surface 1210, the cavity surface 1220, or both. In FIG. 12, the cavity surface element 1270 was modified by moving it away, resulting in a new cavity surface element 1275 offset from the original one. This change defines a new cavity shape 1225 for which a further body insertion motion is possible.

Modifying a single surface element by offsetting it with respect to the contact is by itself is not sufficient. To maintain the connectivity and homogeneity of the surface, the change must be propagated to the adjacent surface elements smoothly. This propagation can be done using standard shape relaxation and optimization techniques. Briefly, the shape relaxation process mimics the physical process of deforming a body surface by applying a force to it. The method takes a force (in this case, the normal vector 1295) and propagates its effects on the surface by displacing surface elements so that they keep connected and comply with the effects of the force. The force applied to each surface element decreases as its distance from the application point of the force increases.

Note that, in general, it is not necessary to remove all interferences. Referring to FIG. 12, of all interferences 1230, it is sufficient to remove the interference of surface pair 1280 to allow body 1200 to continue in its insertion trajectory. In other situations, however, more than one interference has to be removed. The choice of which interference to remove, and which shape should be modified (the body surface, the cavity surface, or both) should be made at each modification step. The choice can be dictated by the human designer or can automatically be made by the method based on diverse shape design and modification criteria. In one embodiment, the shapes can be interactively modified by a human designer using a CAD system by selecting shape patches and deforming them. In another embodiment, the shapes can be modified using design and modification rules previously specified.

The design method is especially suited for designing the prosthetic implant and cavity shapes to achieve the tightest possible fit and determining their insertability.

Figure 13:
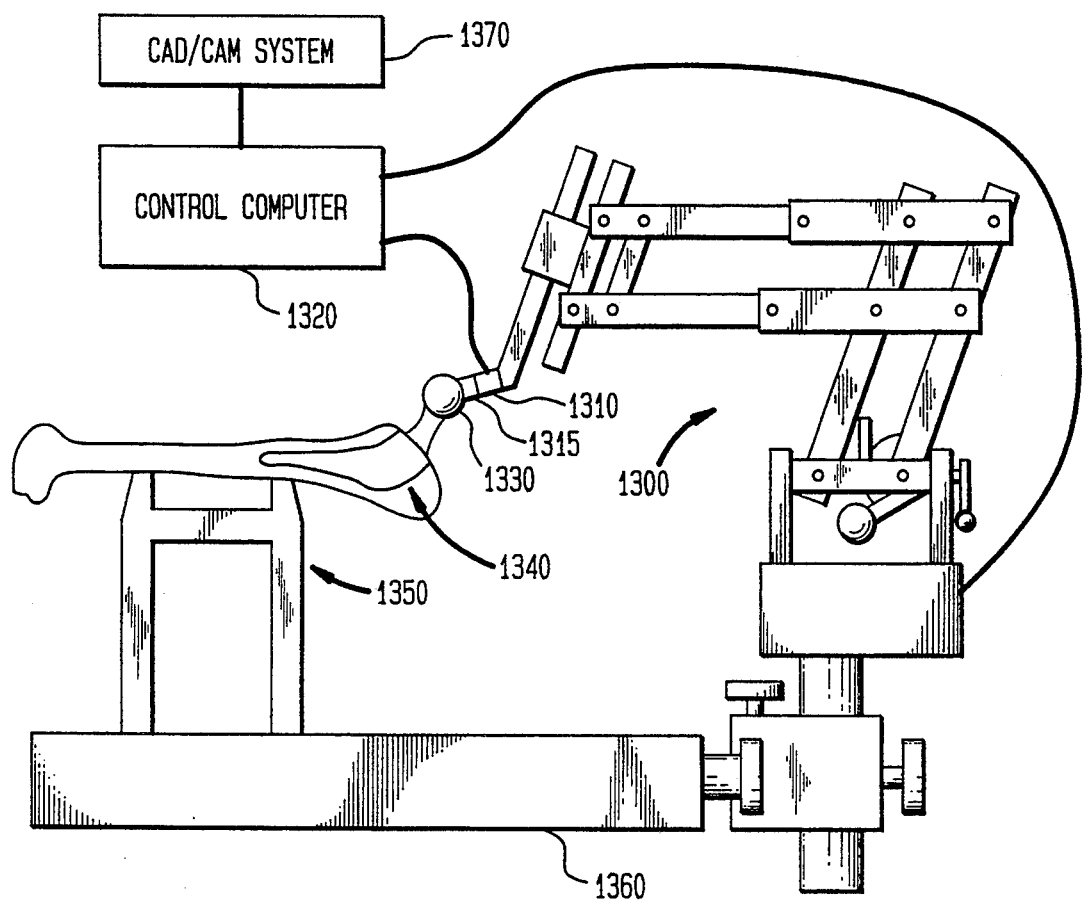
FIG. 13 is a block diagram of a novel apparatus used for the precise interference-free insertion of a tightly fit body into a cavity.

Using the present invention, a novel apparatus can be made for the precise interference-free insertion of a tightly fit body into a cavity. FIG. 13 shows one preferred embodiment of this apparatus, in which the body to be inserted is an orthopedic implant and the cavity is a cavity in a bone.

In this embodiment, the apparatus comprises a robotic manipulator 1300 having at least six degrees of freedom. In one preferred embodiment, manipulator 1300 is a remote-center-of motion manipulator similar to that described by Taylor et al. in U.S. Pat. application Ser. No. 07/968,715, "Remote Center of Motion Robot for Surgery", filed on Oct. 30, 1992, and incorporated herein by reference. Alternatively, any six degree of freedom with an appropriate work volume may be used. Manipulator 1300 is equipped with a six-degree-of-freedom force sensor 1310 in its distal end effector 1315. Control computer 1320 controls the motion of manipulator 1300, and is able to read the forces and torques sensed by force sensor 1310. The end effector 1315 rigidly holds the orthopedic implant 1330 in a known position and orientation relative to the robot, and implant 1330 is to be inserted into bone 1340. A standard fixation device 1350 is used to affix the bone 1340 to operating table 1360. In the embodiment shown, the robot manipulator 1300 is affixed directly to operating table 1360. Alternatively, both operating table and manipulator may be fixed to the floor. Sensing means known to the surgical art are used to locate the bone relative to the robot. One method is described by R. Taylor, et. al. in "Augmentation of Human Precision in Computer-Integrated Surgery" in Innovation et Technologie en Biologie et Medicine, vol 13, Number 4, 1992. The body and cavity shapes are determined by CAD/CAM system 1370, and the method of FIG. 1 is used to determine an interference free nominal trajectory to insert implant 1330 into bone 1340. The control computer 1320 computes the nominal motion of the robot manipulator 1300 to cause the implant 1330 to move through this nominal trajectory relative to bone 1340. The control computer 1320 slowly moves manipulator 1300 through this nominal trajectory while monitoring force sensor 1315. Using methods known in the robotic art, the control computer uses the information from force sensor 1315 to make minor modifications in the trajectory of manipulator 1300 to accommodate small kinematic calibration errors in manipulator 1300, in the sensed relative positions of manipulator 1300 and bone 1340, and minor manufacturing errors in the shape of the implant or bone preparation errors in the shape of the cavity. The control computer 1320 also records all forces encountered during the insertion process, and stops the robot if any force greater than a predetermined threshold value is encountered.

This apparatus has a significant advantage over conventional manual insertion of the implant into the hole, since the robot is able to follow a precisely defined geometric path much more accurately than a human surgeon can, thus guaranteeing that the correct insertion path will be followed. Since a robot may also be used to machine the cavity, no additional sensing of bone position, beyond that required for the cavity machining step, need be performed. Finally, the control computer's ability to stop the process if excessive forces are encountered promotes safety and the ability to record all forces encountered preserves a valuable record for future reference.

The present invention can also be embodied as a novel apparatus for the design and manufacturing of tightly fit insertable body and cavity shapes. The apparatus consists of a computer that drives a numerically controlled (NC) machining device that produces sculptured shapes. Given nominal body and cavity shapes as CAD models, the computer modifies their shapes to guarantee the interference-free insertion of the body inside the cavity. Once the final shapes are obtained, the NC machining device produces the physical shapes. In addition, the computer produces the interference-free trajectory that the body must follow to be inserted in the cavity. To modify the body and cavity shapes, the method 1000 of FIG. 10 as described above can be used. In an alternative embodiment, the NC machining device can be replaced by a 3-dimensional printing device.

There are many advantages of this novel apparatus including: automatically identifying stuck body configurations, identifying the interferences causing them, identifying the parts of the body and cavity surface shapes causing interferences, and modifying these parts to allow the continuation of the body insertion.

FIG. 14 shows a schematic of the proposed apparatus. First, the body and cavity shapes are determined 1410 using the shape design and modification method 1000 of FIG. 10 and a CAD system 1420. Once the shapes are defined, a computer system 1400 downloads the shape descriptions to be manufactured by the NC machining device 1430. The output is a physical body 1450 and/or a physical cavity 1440.

The proposed apparatus is especially suited for designing and manufacturing prosthetic implants and cavity shapes to achieve the tightest possible fit and determining their insertability.

Given this novel disclosure, one skilled in the art could come up with alternative equivalent method of implementing this invention. These alternatives are within the contemplation of the inventors.

We claim:

1. A method for determining an interference-free insertion trajectory of a moving solid body within a cavity, the body being described by a body surface, the cavity being described by cavity surface, the body having configurations with respect to the cavity, the configurations having a position and orientation, and moving the body from a start configuration, through intermediate configurations, to a final configuration, the method comprising the steps of:

(a) describing the body surface by a finite set of body surface elements and the cavity surface by a finite set of cavity surface elements;

(b) determining a set of surface element pairs at the body start configuration, each pair comprising a body surface element and a corresponding cavity surface element, the body and cavity surface elements being paired such that the distance between the body surface element of the pair and the cavity element of the pair is smaller than the distance between the body element of the pair and any other cavity element;

(c) defining a neighborhood for every surface element pair so that the neighborhood contains the body and cavity surface elements in the pair but no other surface elements or parts of surface elements belonging another surface element pair;

(d) determining body motion constraints for every surface element pair so that each paired body and the cavity surface element do not interpenetrate and that the body movement does not cause the body surface element in the pair to leave the neighborhood;

(e) determining an incremental movement of the body so that the incremental movement satisfies the body motion constraints and the incremental movement is along a defined preferred motion direction;

(f) moving the body to a new body configuration by moving the body the incremental body movement; and (g) repeating steps (b) through (f) with the new body configuration until the final body configuration is reached or until a stuck body configuration is attained.

2. A method, as in claim 1, where the start configuration is outside the cavity and the final configuration is a tight fit within the cavity.

3. A method, as in claim 1, where the final configuration is within the cavity and the final configuration is outside the cavity.

4. A method, as in claim 1, where the distance between the cavity and body elements of the pair is smaller than the distance between the cavity element of the pair and any other body element.

5. A method, as in claim 1, where the body surface elements are points on the body surface obtained by sampling the body surface at regular intervals with a grid covering the body surface in its entirety.

6. A method, as in claim 1, where the cavity surface elements are planar facets on the cavity surface obtained by sampling the cavity surface at regular intervals with a grid covering the cavity shape in its entirety.

7. A method, as in claim 1, where the neighborhoods of the surface element pairs are pie-slice shaped volumes each having one wall that is a planar facet defined by a cavity surface element.

8. A method, as in claim 1, where the body surface elements are points on the body surface obtained by sampling the body surface at regular intervals with a grid covering the body shape in its entirety, the cavity surface elements are planar facets on the cavity surface obtained by sampling the cavity surface at regular intervals with a grid covering the cavity shape in its entirety, the neighborhoods of the surface element pairs are pie-slice shaped volumes each having one wall being a planar facet defined by a cavity surface element, and body motion constraints are linearized.

9. A method, as in claim 1, where the incremental movement of the body is defined by a linear function and the preferred motion direction is along an axis of the cavity.

10. A method, as in claim 1, where the incremental movement of the body is optimized by solving an optimization problem in which an objective function is a function describing the preferred motion direction and the constraints are the body motion constraints, the surface element pair neighborhoods, and one or more imposed small motion constraints.

11. A method, as in claim 10, where the direction function is a quadratic function that minimizes body rotations while maximizing the axial motion of the body.

12. A method, as in claim 10, where the direction function is linearized and the optimization problem is linear.

13. A method, as described in claim 12, where the linear optimization problem is solved with a linear programming technique.

14. A method, as in claim 10, where the optimization problem is quadratic.

15. A method, as in claim 14, where the optimization problem is solved with a non-negative least squares technique.

16. A method, as in claim 1, where the body and the cavity are slightly compressible.

17. A method, as in claim 1, where the body motion constraints are augmented with a set of user defined constraints and requirements on the characteristics of the body insertion motion.

18. A method, as in claim 1, where the body is an prosthetic implant and the cavity exists in an anatomical structure.

19. A method for designing and modifying an insertable body shape and a cavity shape and determining an interference-free body insertion trajectory, the body shape being initially described by a nominal body surface, the cavity shape being initially described by nominal cavity surface, and the body being moved from a start configuration, through intermediate configurations, to a final configuration, the method comprising the steps of:
 (a) determining an interference-free insertion trajectory of the moving solid body into the cavity or an intermediate stuck configuration, the determination made by the following steps:
  (1) describing the body shape by a finite set of body surface elements and the cavity shape by a finite set of cavity surface elements;
  (2) determining a set of surface element pairs at the body start configuration, each pair comprising a body surface element and a corresponding cavity surface element, the body and cavity surface elements being paired such that the distance between the body surface element of the pair and the cavity element of the pair is smaller than the distance between the body element of the pair and any other cavity element;
  (3) defining a neighborhood for every surface element pair so that the neighborhood contains the body and cavity surface elements in the pair but no other surface elements or parts of surface elements belonging another surface element pair;
  (4) determining body motion constraints for every surface element pair so that each paired body and the cavity surface element do not interpenetrate and that the body movement does not cause the body surface element in the pair to leave the neighborhood;
  (5) determining an incremental movement of the body so that the incremental movement satisfies the body motion constraints and the incremental movement is along a defined preferred motion direction;
  (6) moving the body to a new body configuration by moving the body the incremental body movement; and
  (7) repeating steps (2) through (6) with the new body configuration until the final body configuration is reached or until a stuck body configuration is attained;
 (b) determining if the body has reached its final configuration or is in a stuck configuration;
 (c) identifying the interferences between the body and the cavity that prevent the body from continuing on its insertion trajectory when the body is stuck;
 (d) modifying the body and cavity shapes to remove the interferences so as to allow the body to continue in its insertion trajectory; and
 (e) repeating steps (a) through (d) until the body reaches its final configuration inside the cavity.

20. A method, as in claim 19, where the nominal body and cavity shapes are derived from a shape template and a shape template complement.

21. A method, as in claim 19, where the body and cavity modifications are dictated by a human designer after the interferences and the body and cavity surfaces causing them have been identified.

22. A method, as in claim 19, where the body and cavity modifications are automatically made based on diverse shape design and modification criteria.

23. A method, as in claim 19, where the body and cavity modifications are automatically made using shape relaxation techniques.

24. A method, as in claim 19, where the interferences between the body and the cavity are identified by optimizing a function describing a preferred direction of body motion.

25. A method, as in claim 19, where the body is an prosthetic implant and the cavity exists in an anatomical structure.

26. A method for inserting without interferences a moving solid body into a cavity by having a computer-controlled end effector follow an interference-free body insertion trajectory, the body being described by a body surface, the cavity being described by cavity surface, and the body being moved from a start configuration, through intermediate configurations, to a final configuration, the method comprising the steps of:
- (a) describing the body surface shape by a finite set of body surface elements and the cavity surface shape by a finite set of cavity surface elements;
- (b) determining a set of surface element pairs at the body start configuration, each pair comprising a body surface element and a corresponding cavity surface element, the body and cavity surface elements being paired such that the distance between the body surface element of the pair and the cavity surface element of the pair is smaller than the distance between the body surface element of the pair and any other cavity surface element;
- (c) defining a neighborhood for every surface element pair so that the neighborhood contains the body and cavity surface elements in the pair but no other surface elements or parts of surface elements belonging another surface element pair;
- (d) determining body motion constraints for every surface element pair so that the body and the cavity do not interpenetrate and the body movement does not cause the body surface element in the pair to leave the neighborhood;
- (e) determining an incremental movement of the body so that the incremental movement satisfies the body motion constraints and the incremental movement is along a defined preferred motion direction;
- (f) simulate moving the body to a new configuration an amount of the incremental body movement;
- (g) repeating steps (b) through (f) with the new body configuration until the final body configuration is reached and an interference-free trajectory is defined or until a stuck body configuration is attained; and
- (h) executing the interference-free body insertion trajectory on the end effector.

27. A method, as in claim 26, where the body is a prosthetic implant and the cavity exists in an anatomical structure.

28. A method, as in claim 26, having the additional steps of:
- (j) monitoring any insertion forces on the body; and
- (k) modifying the trajectory base on the monitored forces.

29. An apparatus for the precise interference-free insertion of a body into a cavity, comprising:
- (a) a computer-controlled positioning and manipulation device to insert the body into the cavity;
- (b) a CAD system to define the body and cavity shapes; and
- (c) a computer that determines the interference-free body insertion trajectory from the body and cavity shapes defined by the CAD system and drives the positioning and manipulation device along the trajectory, the trajectory determined by the following steps:
  - (1) describing a body surface by a finite set of body surface elements and a cavity surface by a finite set of cavity surface elements;
  - (2) determining a set of surface element pairs at the body start configuration, each pair comprising a body surface element and a corresponding cavity surface element, the body and cavity surface elements being paired such that the distance between the body surface element of the pair and the cavity element of the pair is smaller than the distance between the body element of the pair and any other cavity element;
  - (3) defining a neighborhood for every surface element pair so that the neighborhood contains the body and cavity surface elements in the pair but no other surface elements or parts of surface elements belonging another surface element pair;
  - (4) determining body motion constraints for every surface element pair so that each paired body and the cavity surface element do not interpenetrate and that the body movement does not cause the body surface element in the pair to leave the neighborhood;
  - (5) determining an incremental movement of the body so that the incremental movement satisfies the body motion constraints and the incremental movement is along a defined preferred motion direction;
  - (6) moving the body to a new body configuration by moving the body the incremental body movement; and
  - (7) repeating steps (2) through (6) with the new body configuration until the final body configuration is reached or until a stuck body configuration is attained.

30. An apparatus as in claim 29, where the end effector is a robotic arm specifically designed for the insertion task, the body is a prosthetic implant, and the cavity exists in an anatomical structure.

31. An apparatus for the design and manufacturing of insertable body and cavity shapes, comprising:
- (a) a numerically-controlled machining device for the manufacturing of the body and cavity;
- (b) a CAD system to define and modify the body and cavity shapes; and
- (c) a computer for determining an interference-free body insertion trajectory and designing and modifying the insertable body and cavity shapes to conform to the trajectory, the trajectory determined by the following steps:
  - (1) describing the body shape by a finite set of body surface elements and the cavity shape by a finite set of cavity surface elements;
  - (2) determining a set of surface element pairs at the body start configuration, each pair comprising a body surface element and a corresponding cavity surface element, the body and cavity surface elements being paired such that the distance between the body surface element of the pair and the cavity element of the pair is smaller than the distance between the body element of the pair and any other cavity element;
  - (3) defining a neighborhood for every surface element pair so that the neighborhood contains the body and cavity surface elements in the pair but no other surface elements or parts of surface elements belonging another surface element pair;
  - (4) determining body motion constraints for every surface element pair so that each paired body and the cavity surface element do not interpenetrate and that the body movement does not cause the body surface element in the pair to leave the neighborhood;
  - (5) determining an incremental movement of the body so that the incremental movement satisfies the body motion constraints and the incremental movement is along a defined preferred motion direction;

(6) moving the body to a new body configuration by moving the body the incremental body movement; and (7) repeating steps (2) through (6) with the new body configuration until the final body configuration is reached or until a stuck body configuration is attained.

32. An apparatus, as in claim 31, where the machining device is a 3-dimensional printing device.

33. An apparatus, as in claim 31, where the body is a prosthetic implant and the cavity exists in an anatomical structure.

* * * * *